US006916917B1

(12) United States Patent
Baltimore et al.

(10) Patent No.: US 6,916,917 B1
(45) Date of Patent: Jul. 12, 2005

(54) CHIMERIC PRO-CASPASES AND METHODS OF USING SAME

(75) Inventors: David Baltimore, Pasadena, CA (US); Xiaolu Yang, Philadelphia, PA (US); Howard Y. Chang, Cambridge, MA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/441,926

(22) Filed: Nov. 17, 1999

Related U.S. Application Data

(60) Provisional application No. 60/108,873, filed on Nov. 17, 1998.

(51) Int. Cl.$^7$ .............................................. C07H 21/04
(52) U.S. Cl. ......................... 536/23.4; 530/350; 514/44
(58) Field of Search ....................... 536/23.4; 530/350; 514/44

(56) References Cited

U.S. PATENT DOCUMENTS 4,889,806 A * 12/1989 Olson et al. ............. 435/172.3
5,837,837 A * 11/1998 Hunter et al. .............. 536/23.1

OTHER PUBLICATIONS

Miller FASEB .j, 9:190–199, 1995.*
Deonarian. Expert. Opin. Ther. Pat. 8. 53–69, 1998.*
Verma .Nature, 389: 239–242, 1997.*
Crystal Science 270 : 404–410, 1995.*
Meergans, T. Brocheru J. 349(1):135–140, 2000.*
Muzio. J. Biol. Chem, 273(5): 2926–2930, 1998.*
Masako, U. Intl. J. Oncol. 20(3):617–22, 2002.*
Browes, C. FEBS letters, 497(1):20–5, 2001.*
Bider, M D J.B.C. 271:31996–2001, 1996.*
Grika. Science, 278: 1041–1042, 1997.*
Jain Sci Amer 271:58–65, 1994.*
Curti. Crit. Rev. Oncol./Hematol. 14:29–39, 1993.*
Hartwell. Science 278:1064–1068, 1997.*
Yang, X. Mol. Cell. 1:319–325, 1998.*
Sambrook, J. Mol. Cloning, Cold Spring Harbor Press, Cold Spring Harbor, p. 16.3–16.4, 16.26–16.27, 1989.*
Boehringer Mannheim, Biochemicals Catalog, p. 93, 1994.*
Chang, D. W., et al., "Oligomerization Is a General Mechanism for the Activation of Apoptosis Initiator and Inflammatory Procapases," *The Journal of Biological Chemistry*, vol. 278, No. 19, 2003, pp. 16466–16469.
Hu, Y., et al., "WD–40 Repeat Region Regulates Apaf–1 Self–association and Procaspase–9 Activation," *The Journal of Biological Chemistry*, vol. 273, No. 50, Dec. 11, 1988, pp. 33489–33494.

Martin, D.A. et al., "Membrane Oligomerization and Cleavage Activates the Caspase–8 (FLICE/MACHα1) Death Signal," *The Journal of Biological Chemistry*, vol. 273, No. 8, Feb. 20, 1998, pp. 4345–4349.
Srinivasula, S.M., et al., "Autoactivation of Procaspase–9 by Apaf–1–Mediated Oligolerization," *Molecular Cell*, vol. 1, Jun., 1998, pp. 949–957.
Cohen, G.M., "Caspases: the executioners of apoptosis," *Biochem. J.* 326:1–16 (1997).
Schwarze, et al, "In Vivo Protein Transduction: Delivery of a Biologically Active Protein into the Mouse," *Science* 285:1569–1572(1999).
Thornberry and Lazebnik, "Caspases: Enemies Within," *Science* 281:1312–1316 (1998).
Vocero–Akbani, et al., "Killing HIV–infected cells by transduction with an HIV protease–activated caspase–3 protein," *Nature Medicine* 3(1):29–33(1999).
Yang, et al., "Autoproteolytic Activation of Pro–Caspases by Oligomerization," *Molecular Cell* 1:319–325 (1998).
Yang, et al., "Essential Role of CED–4 Oligomerization in CED–3 Activation and Apoptosis," *Science* 281:1355–1357 (1998).

* cited by examiner

*Primary Examiner*—Susan Ungar
*Assistant Examiner*—Minh-Tam Davis
(74) *Attorney, Agent, or Firm*—Gray Cary Ware & Freidenrich, LLP

(57) ABSTRACT

The present invention relates to a chimeric pro-caspase, which contains a pro-caspase domain and an oligomerizing domain. The invention also relates to an antibody that reacts specifically with a chimeric pro-caspase. In addition, the invention further relates to a polynucleotide encoding a chimeric pro-caspase, and to nucleotide sequences, which can hybridize specifically with a polynucleotide encoding a chimeric pro-caspase. The present invention also relates to a method of inducing apoptosis in a cell by providing a chimeric pro-caspase in the cell, wherein the chimeric pro-caspase includes a pro-caspase domain and an oligomerizing domain, whereby the chimeric pro-caspase forms an oligomer in the cell, thereby activating caspase activity of the chimeric pro-caspase and inducing apoptosis in the cell. The present invention further relates to a method of reducing the severity of a pathologic condition in a subject, by providing cells of the subject that are involved in the pathologic condition with a chimeric pro-caspase comprising a pro-caspase domain and an oligomerizing domain, whereby the chimeric pro-caspase forms an oligomer in the cells, thereby activating caspase activity of the chimeric pro-caspase, inducing apoptosis in the cells, and reducing the severity of the pathologic condition in the subject.

10 Claims, 6 Drawing Sheets

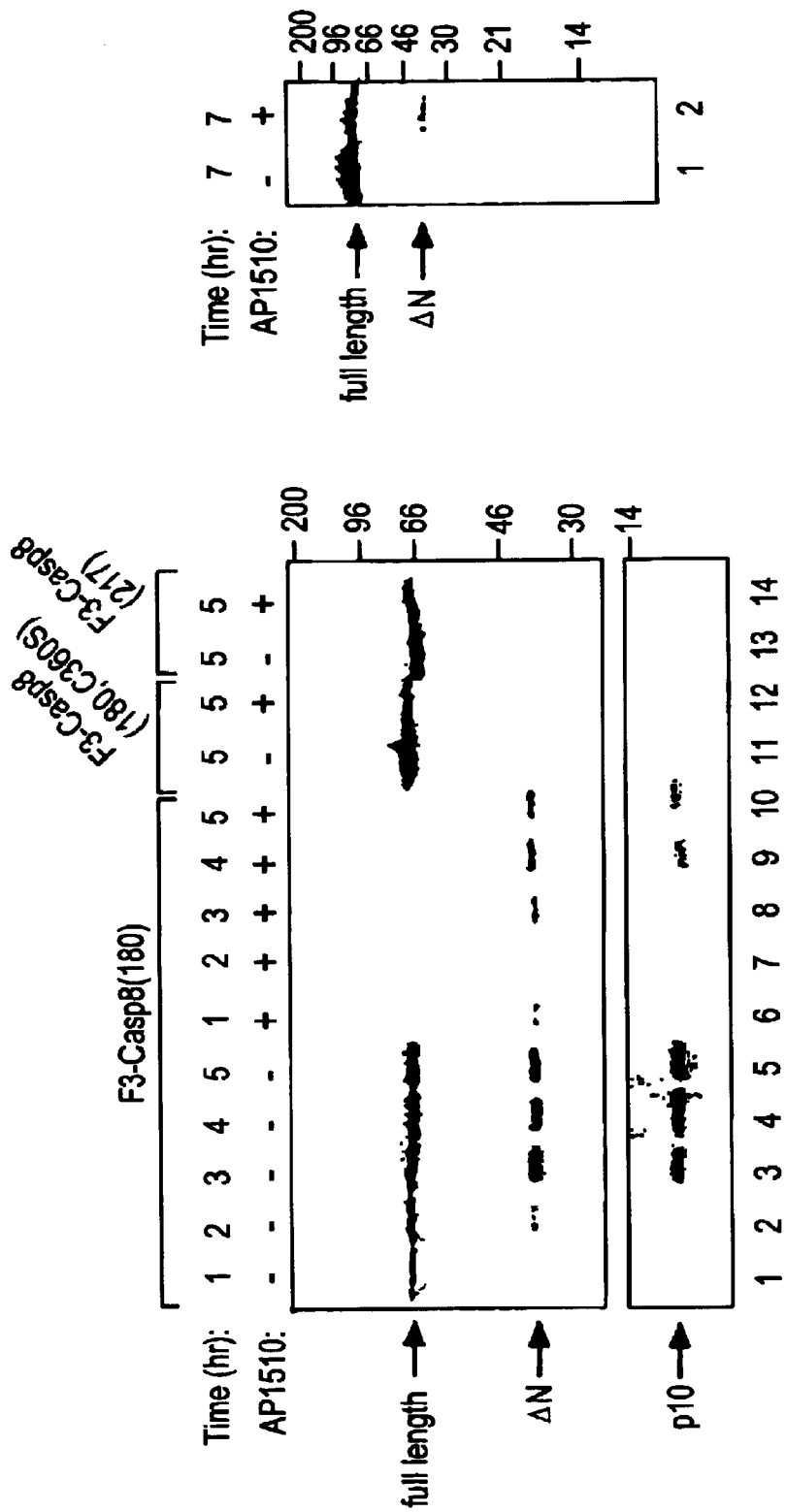

CHIMERIC PRO-CASPASES AND METHODS OF USING SAME

This application claims the benefit of priority of U.S. provisional patent application Ser. No. 60/108,873, filed Nov. 17, 1998, the entire contents of which is incorporated herein by reference.

This invention was made in part with government support under Grant No. RO1 CA51462 awarded by the National Institutes of Health. The government has certain rights in this invention.

BACKGROUND OF THE INVENTION

1. Field of the Invention

The present invention relates generally to molecular biology and medicine and more specifically to pro-caspases that have been modified to facilitate directed oligomerization, and to methods of using such modified pro-caspases for inducing apoptosis in a cell.

2. Background Information

In essentially all self-renewing tissues, a balance is struck between cell production by mitosis and cell loss due to programmed cell death, thereby maintaining total cell numbers within a physiologically appropriate range. In pathological conditions, however, the balance in cell production and cell loss can be disrupted. In cancer, for example, an increased amount of cell production due to a shortened cell cycle time or to a decreased amount of cell death can occur due to dysregulation of a programmed cell death pathway, resulting in growth of a tumor. Dysregulation of apoptosis also can occur, for example, in neurodegenerative diseases, in which neurons die prematurely, and induction of apoptosis can figure prominently in the pathophysiology of diseases associated with viral infection.

In multicellular organisms, homeostasis is maintained by balancing the rate of ell proliferation against the rate of cell death. Cell proliferation is influenced by numerous growth factors and the expression of proto-oncogenes, which typically encourage progression through the cell cycle. In contrast, numerous events, including the expression of tumor suppressor genes, can lead to an arrest of cellular proliferation.

In differentiated cells, a particular form of programmed cell death, apoptosis, is carried out when an internal suicide program is activated. This program can be initiated by a variety of external signals as well as signals that are generated within the cell, for example, in response to genetic damage. For many years, the magnitude of apoptotic cell death was not appreciated because the dying cells are quickly eliminated by phagocytes, and in the absence of an inflammatory response.

Various diseases, including, for example, cancer, inborn errors of metabolism, and neurodegenerative diseases have been refractory to treatment. Recently, however, gene therapy has begun to emerge as a viable means to treat such diseases at the cellular level. Although clinical trials of gene therapy protocols have yet to produce statistically significant results, positive results obtained in patients treated by gene therapy cannot be ignored, particularly since gene therapy generally has been practiced on patients that have failed more conventional treatment protocols.

Although gene therapy holds great promise to alleviate and cure various inherited and acquired diseases, it must be proven not only efficient, but also safe, in order to become a routine clinical procedure. Unfortunately, genetically manipulated cells can acquire unwanted properties and become deleterious to the host due, for example, to insertion of an introduced gene into an otherwise normal gene in the host cell, thus disrupting the function of the normal gene. A method that ablates such cells can provide a safeguard against unwanted deleterious effects and, therefore, is highly desired. Ideally, such a system should effectively and specifically induce apoptosis, a physiologic form of cell death that rids the body of a cell without eliciting a harmful inflammatory response.

The mechanisms that mediate apoptosis have been studied intensively, and involve the activation of endogenous proteases, the loss of mitochondrial function, and the appearance of structural changes such as disruption of the cytoskeleton, cell shrinkage, membrane blebbing, and nuclear condensation due to degradation of DNA. The various signals that trigger apoptosis are thought to bring about these events by converging on a common cell death pathway that is regulated by the expression of genes that are highly conserved evolutionarily. However, while numerous genes have been identified as involved in process of apoptosis, the mechanisms by which the products of these genes interact to execute the apoptotic program is not well understood.

SUMMARY OF THE INVENTION

The present invention is based on the seminal discovery that oligomerization is sufficient to initiate pro-caspase processing in vivo and in vitro and to activate their cell death activity. Given this observation, the inventors have produced chimeric pro-caspases, which contain a pro-caspase domain and an oligomerizing domain. In one embodiment, the pro-caspase domain is pro-caspase-8 or a peptide portion of pro-caspase-8, which has caspase-8 activity potential. The pro-caspase domain also can be a pro-caspase form of an initiator caspase such as pro-caspase-1, or a peptide portion of a pro-caspase having initiator caspase activity potential. The oligomerizing domain can be a polypeptide that spontaneously forms an oligomer, or that forms an oligomer in the presence of an agent that induces oligomerization. In one embodiment, the oligomerizing domain is an FK506 binding protein (FKBP), or an FK506 binding domain of FKBP, which forms an oligomer in the presence of a specific dimerizing agent. The oligomerizing domain also can be a polypeptide that interacts specifically with cellular protein in the cell, or the cellular protein binding domain of the polypeptide. In one embodiment, the oligomerizing domain is a Ras-associating domain of a Raf protein. In still another embodiment, the oligomerizing domain is a guanine exchange factor domain, which interacts specifically with a Ras cellular protein. A chimeric pro-caspase can contain one or more additional domains, including, for example, a protein transduction domain such as the human immunodeficiency virus TAT protein transduction domain, or a cell compartmentalization domain.

The present invention also relates to an antibody that reacts specifically with a chimeric pro-caspase. Such an antibody is characterized, in part, in that does not react substantially with an isolated pro-caspase domain, oligomerizing domain or other domain of a chimeric pro-caspase and, therefore, can distinguish the presence of a chimeric pro-caspase from, for example, a naturally occurring pro-caspase, including the pro-caspase from which the pro-caspase domain of the chimeric pro-caspase was derived. Also provided are kits containing such an antibody.

The present invention further relates to a polynucleotide encoding a chimeric pro-caspase of the invention. The polynucleotide can be contained in a vector, which can be a cloning vector or an expression vector, and the vector can be contained in a host cell. In one embodiment, a polynucleotide encoding a chimeric pro-caspase is contained in a viral expression vector. In addition, the invention relates to oligonucleotides, which can hybridize specifically with a polynucleotide encoding a chimeric pro-caspase. Such oligonucleotides are characterized, at least in part, in that they do not hybridize substantially to nucleic acid molecules encoding individual domains of the chimeric pro-caspase.

The present invention also relates to a method of inducing apoptosis in a cell by providing a chimeric pro-caspase in the cell, wherein the chimeric pro-caspase includes a pro-caspase domain and an oligomerizing domain. According to a method of the invention, the chimeric pro-caspase forms an oligomer in the cell, thereby activating caspase activity of the chimeric pro-caspase and inducing apoptosis in the cell. Such a method can be used for inducing apoptosis in a cell in vitro, or for inducing apoptosis in a cell in vivo.

A pro-caspase domain of a chimeric pro-caspase useful in a method of the invention can be a pro-caspase form of an initiator caspase or a peptide portion of a pro-caspase having initiator caspase activity potential. In one embodiment, the pro-caspase domain is pro-caspase-8 or a peptide portion of pro-caspase-8, which has caspase-8 activity potential. The oligomerizing domain of a chimeric pro-caspase can be a domain that oligomerizes spontaneously in a cell, or can be a domain that is induced to form an oligomer in the presence of an agent that mediates oligomerization. In one embodiment, the oligomerizing domain is FKBP, and the chimeric pro-caspase is induced to form an oligomer by contacting the cell with an agent that induces oligomerization of FKBPs, thereby inducing apoptosis in the cell. In another embodiment, the oligomerizing domain is a polypeptide that interacts specifically with cellular protein in the cell, for example, a Raf domain, which interacts specifically with Ras.

A method of the invention can be performed by introducing a polynucleotide encoding the chimeric pro-caspase into the cell, and expressing the encoded chimeric pro-caspase. In performing such a method, the polynucleotide encoding the chimeric pro-caspase can be contained in an expression vector, for example, a viral expression vector. A method of the invention also can be performed by contacting the cell with the chimeric pro-caspase, which can comprise a protein transduction domain such as the human immunodeficiency virus TAT protein transduction domain, whereby the chimeric pro-caspase is translocated into the cell due to the presence of the protein transduction domain.

The present invention further relates to a method of reducing the severity of a pathologic condition in a subject, by providing cells involved in the pathologic condition in the subject with a chimeric pro-caspase comprising a pro-caspase domain and an oligomerizing domain, whereby the chimeric pro-caspase can oligomerize in the cell, thereby activating caspase activity of the chimeric pro-caspase, which induces apoptosis in the cells and reduces the severity of the pathologic condition in the subject. The pathologic condition can be characterized, for example, by an undesirably high level of cell proliferation or by an undesirably low level of programmed cell death. In one embodiment, the pathologic condition is a neoplasia, which can be a benign neoplasia or a malignant neoplasia. In another embodiment, the pathologic condition is an autoimmune disease, wherein the cells associated with the pathologic condition are immunocytes.

A method of the invention can be performed by providing cells of the subject that are involved in the pathologic condition with a chimeric pro-caspase ex vivo, then administering surviving cells to the subject, thereby reducing the severity of the pathologic condition in the subject. A method of the invention also can be performed by providing cells of the subject that are involved in the pathologic condition with a chimeric pro-caspase in vivo, whereby the chimeric pro-caspase forms an oligomer in the cells, thereby activating caspase activity of the chimeric pro-caspase, inducing apoptosis in the cells, and reducing the severity of the pathologic condition in the subject The chimeric pro-caspase, or a polynucleotide encoding the chimeric pro-caspase, can be administered to the site of the pathologic condition, or by any method that provides the cells to be treated with the chimeric pro-caspase. Accordingly, the invention also relates to pharmaceutical compositions, which can contain a chimeric pro-caspase or a polynucleotide encoding a chimeric pro-caspase.

BRIEF DESCRIPTION OF THE FIGURES

FIG. 1A is a schematic diagram of the FKBP fusions of pro-caspase-8 (Fkp), FK506 binding protein FKBP12; (DED), death effector domain; (p18) and (p10), subunits that form caspase-8; (d), aspartic acids at the cleavage sites for the generation of p18 and p10; (*), the active site cysteine-to-serine mutation. cSrc myristylation signal (M) and HA and FLAG tags are also indicated.

FIG. 1B shows apoptosis induced by pro-caspase-8 fusion proteins. HeLa cells were transfected with 0.125 µg of each Fkp-Casp8 plasmid and 0.25 g of pRK-crmA as indicated. Percentages of specific apoptosis were determined as described in Example I.

FIG. 2A shows caspase-8(180)-induced apoptosis requires oligomerization and intrinsic protease activity. HeLa cells were transfected with 0.125 µg of Fkp3, Fkp3-Casp8(180) or Fkp3-Casp8(180,C360S), together with 0.25 µg of pRK-crmA or 0.125 µg of Fkp3 as indicated. Treatment of AP1510 (concentration indicated) and FK506 (50 nM) was done for 10 hr as described in Example I.

FIG. 2B shows pro-caspase processing is required for oligomerization-induced apoptosis. HeLa cells were transfected with 0.125 µg of Fkp3, Fkp3-Casp8(206) or Fkp3-Casp8(217). AP1510 treatment was as described in FIG. 2A.

FIG. 3A is a schematic diagram of pro-caspase-1, -3 and -8 fusions with the murine Fas extracellular domain. The fusion constructs contained either pro-caspase-8 (amino acids 182–479), full length murine pro-caspase-1, or full length human pro-caspase-3—as well as the corresponding catalytic Cys-to-Ser mutations (not shown)—fused to the extracellular and transmembrane domain of murine Fas (FasEC). The leader peptide (L) and transmembrane domain (TM) of murine Fas, FLAG tag, and the large and small subunits of each caspase are indicated.

FIG. 3B shows FasEC-mediated oligomerization of pro-caspase-8 activates its apoptotic activity. HeLa cells were transfected with FasEC (25 ng), FasEC-Casp8(182) (25 ng), FasEC-Casp8(192, C360S) (125 ng), or pEBB-mFas (250 ng), together with pRK-crmA (250 ng) as indicated. Jo2 treatment and X-gal staining are as described in Example I.

FIG. 3C shows FasEC-mediated oligomerization activates the apoptotic activity of pro-caspase-1 but not procaspase-3. Experiments were done as described above. The amount of plasmids used for each transfection was 12.5 ng for FasEC and FasEC-Casp1; 125 ng for FasEC-Casp1 (C284S), FasEC-Casp3, and FasEC-Casp3(C163S); and 250 ng for pRK-crmA.

FIGS. 4A and 4B show pro-caspase processing in transfected cells.

FIG. 4A shows pro-caspase processing induced by oligomerization. 293T cells were transfected with 1 µg of the indicated Fkp3-fusion expression constructs. Vehicle or 1 mM AP1510 was added 11 hr after transfection, and cell extracts were made after the indicated times and immunoblotted for FLAG.

FIG. 4B shows processing in the presence of crmA. 293T cells were cotransfected with 1 µg of Fkp3-Casp8(180) and 1 µg of pRK5-crmA. Drug treatment, cell extracts, and FLAG immunoblot were performed as in FIG. 4A.

FIG. 5A shows pro-caspase processing induced by oligomerization. The processing reaction was carried out with in vitro-translated, $^{35}$S-labeled FKBP fusions as described in Example I and visualized by SDS-PAGE and autoradiography.

FIG. 5B shows a time course of pro-caspase processing. The deduced domain structure of the indicated bands is shown on the right.

DETAILED DESCRIPTION OF THE INVENTION

Figure 1A:
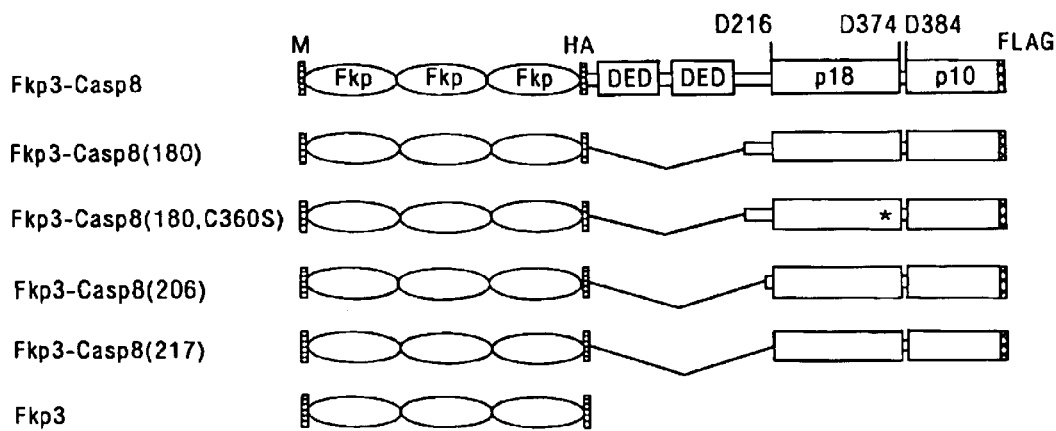
FIGS. 1A and 1B show the apoptotic activity of FKBP fusions of full length and mutant pro-caspase-8.

The present invention provides a chimeric pro-caspase, which contains a pro-caspase domain and an oligomerizing domain. As disclosed herein, oligomerization of pro-caspases induced proteolytic generation of mature caspase subunits and activated their cell death activity (see, also, Yang et al., Mol. Cell 1:319–325 (1998a), which is incorporated herein by reference). The present invention provides chimeric pro-caspases, which can oligomerize in a cell, thereby activating apoptosis. Chimeric pro-caspases can be useful as therapeutic agents for treating, for example, a cell proliferative disorder such as a cancer because they directly connect the fundamental defect in the disorders (the biochemical signals that allow the pathologic cells to grow) to the therapeutic goal (killing the pathologic cells). Thus, the invention also provides methods of reducing the severity of a pathologic condition by providing chimeric pro-caspases in cells involved in the condition, whereby the chimeric pro-caspases oligomerize and activate apoptosis of the cells.

Apoptosis (programmed cell death) is a tightly controlled system for ridding the body of cells that are unnecessary or undesirable. In general, apoptosis is induced by a signal that generates a cascade of events culminating in death of a cell and, when occurring in vivo, in removal of the cell from the body without the generation of an inflammatory response. A prime example of a caspase cascade is found in apoptosis induced by the cell death receptor Fas (see Nagata, Cell 88:355–365 (1997)). The intracellular tail of Fas interacts with the adaptor protein, FADD, which contains a death effector domain (DED) that interacts with homologous DED domains on pro-caspase-8 (FLICE/MACH/Mch5). Recruitment of pro-caspase-8 to the receptor completes the death-inducing signaling complex (DISC) and activates pro-caspase-8. Active DISC formation then leads to the sequential activation of caspase-1-like and caspase-3-like activities.

Several polypeptides can form a complex that transmits an apoptotic signal when the Fas/APO-1 receptor is bound (Boldin et al., Cell 85:803–815 (1996); Muzio et al., Cell 85:817, 1996). The Fas/APO receptor ("CD95") is present on the surface of a wide variety of cells (Boldin et al., supra, 1996; Muzio et al., supra, 1996). The Fas/APO-1 receptor and the TNF receptor are members of the TNF/nerve growth factor receptor family and both share a region of homology designated the "death domain" (Boldin et al., supra, 1996; Muzio et al., supra, 1996). The death domain of the Fas/APO1 receptor interacts with FADD (Fas-associating protein with death domain; also known as MORT1) and RIP (receptor interacting protein), forming a complex that, when joined by Caspase-8, constitutes the Fas/APO-1 death-inducing signaling complex (Boldin et al., supra, 1996; Muzio et al., supra, 1996).

The interaction between Fas/APO-1 and FADD is mediated by their respective C-terminal death domains (Chinnaiyan et al., Cell 81:505–512 (1995)). Caspase-8 contains two N-terminal stretches of approximately 60 amino acids that are homologous to the DED of FADD (Muzio et al., supra, 1996). The remainder of caspase-8 is highly homologous to the ICE/CED-3 family of cysteine proteases, which induce cell death if overexpressed. A number of forms of caspase-8 have been described (Boldin et al., supra, 1996).

The mammalian caspases are a family of cysteine proteases that cleave after an aspartate residue and have a central role in the programmed cell death pathway (see Henkart, Immunity 4:195–201 (1996); Salvesen and Dixit, supra, 1997). Caspase-1 also processes pro-interleukin-1 and has an important role in inflammation. Caspases normally exist in the cytoplasm as inactive pro-caspases (Salvesen and Dixit, Cell 91:443–446 (1997); Thornberry and Lazebnik, Science 281:1312–1316 (1998); Alnemri et al., Cell 87:171 (1996), each of which is incorporated herein by reference). Apoptotic signals convert the precursors of a first subfamily of caspases, the "initiator" caspases, to mature caspases, which then activate a second subfamily of caspases, the "executioner" caspases, which cleave cellular substrates, thereby executing apoptosis. As such, the activation of initiator caspases is a key step that decides the fate of the cell and is subjected to intricate regulation.

Pro-caspases consist of a prodomain and a protease domain. The protease domain contains a large subunit and a small subunit, and two large subunits and two small subunits interact to form a tetrameric mature caspase. Cleavage of the protease domain at critical aspartic acid residues releases the large and small subunits. Initiator caspases generally have a long prodomain, which interacts with upstream regulators, whereas executioner caspases generally contain a short prodomain, which is cleaved by mature initiator caspases.

The tetrameric structure of a mature caspase, which consists of two large subunits of approximately 20 kDa surrounding two small subunits of approximately 10 kDa, was determined based on the crystal structures of caspase-1 and caspase-3 (Henkart, supra, 1996; Salvesen and Dixit, supra, 1997). The protease active site includes residues from both subunits; the large subunit contains a conserved pentapeptide (see Cohen, *Biochem. J.* 326:1–16 (1997), which is incorporated herein by reference). Both the large and small subunits are generated from a single pro-caspase polypeptide by proteolytic cleavages. These cleavages separate the C-terminal protease domains from the N-terminal prodomains of various lengths and also separate the two protease subunits.

Mature caspases often can process their own precursors as well as other procaspases in vitro, suggesting that caspases may function in a cascade (Porter et al., *BioEssays* 19:501–507 (1997); Salvesen and Dixit, supra, 1997). Caspases have been conceptually divided into initiators and executioners based on their potential roles in a cascade (Salvesen and Dixit, supra, 1997). Caspase-3 or caspase-3-like proteases are responsible for the proteolytic cleavage of many death substrates, which leads to the morphological changes and DNA fragmentation that are the hallmarks of apoptosis (Porter et al., supra, 1997). As such, caspase-3 is regarded as an executioner caspase (Salvesen and Dixit, supra, 1997). Consistent with this hypothesis, pro-caspase-3 has a very short prodomain and can be proteolytically activated by an upstream caspase (Muzio et al., *J. Biol. Chem.* 272:2952–2956 (1997)).

Prior to the present disclosure, it was not clear how a pro-caspase such as pro-caspase 8, which initiates a cascade of caspase activation, becomes activated. Several mechanisms have been postulated, including the removal of an inhibitor (Fraser and Evan, *Cell* 85:781–784 (1996)); the presence of an inducible cofactor (such as CAP3 in DISC Medema et al., *EMBO J.* 16:2794–2804 (1997)); or processing of pro-caspases by noncaspases (Zhou and Salvesen, *Biochem. J.* 324:361–364 (1997)). As disclosed herein, oligomerization of pro-caspases leads to self-cleavage, which generates mature caspase enzymes and activates their cell death activity (see, also, Yang et al., supra, 1998a). A major group of cell death activators, including Apaf1 and CED-4, form homo-oligomers, which, in turn, can induce oligomerization of pro-caspases that associate with them. In comparison, the Bcl-2 family of proteins exert their anti-apoptotic function by inhibiting the oligomerization of CED-4 and Apaf-1 (see Yang et al., *Science* 281:1312–1316 (1998b), which is incorporated herein by reference).

The present invention provides chimeric pro-caspases, which can oligomerize and activate caspase activity in a cell, and methods of using such chimeric pro-caspases to selectively induce apoptosis in a cell. A chimeric pro-caspase is a non-naturally occurring molecule that is engineered to contain at least a first domain, which has caspase activity potential, and a second domain, which has oligomerizing activity. Upon forming an oligomer, the caspase activity of the chimeric pro-caspase is activated. As used herein, the term "caspase activity" refers to an ability to cleave a polypeptide at an aspartic acid residue and initiate or propagate an apoptotic pathway. In addition, the term "caspase activity potential," when used in reference to a pro-caspase domain component of a chimeric pro-caspase, means that the domain has a latent ability to cleave a polypeptide at an aspartate residue and initiate or propagate the apoptotic pathway; the latent activity is manifest as caspase activity upon oligomerization. Caspase activity potential of a chimeric pro-caspase can be identified by detecting caspase activity upon oligomerization of the chimeric pro-caspase.

Methods for detecting caspase activity are disclosed herein or otherwise well known in the art (see Example I). Such methods include, for example, detecting characteristic structural changes in a cell such as disruption of the cytoskeleton, cell shrinkage, membrane blebbing, or nuclear condensation due to degradation of DNA; or by detecting the characteristic nucleosomal degradation pattern of genomic DNA by gel electrophoresis, or the like. Commercially available assays to detect, for example, annexin V binding to a cell in conjunction with propidium iodide exclusion; mitochondrial membrane potential disruption; poly (ADP-ribose) polymerase activity; and the like (R & D Systems, Minneapolis Minn.; Alexis Biochemicals, San Diego Calif.) also can be used to detect caspase activity.

Caspase activity is activated upon oligomerization of a chimeric pro-caspase. As used herein, the term "oligomer" refers to two or more molecules that interact specifically with each other to form a complex. An oligomer can be a homo-oligomer, wherein each of the interacting molecules is the same (for example, two identical chimeric pro-caspases), or a hetero-oligomer, wherein the interacting molecules include at least two molecules that are different from each other. For convenience, the molecules that interact to form an oligomer are referred to as "binding partners," at least one of which is a chimeric pro-caspase. It should be recognized, however, that, in some embodiments of the invention, oligomerization is not due to a direct interaction of the binding partners but, instead, is mediated by an agent that induces oligomerization. For purposes of this disclosure, such an agent, although a component of the oligomer, is not considered to be encompassed within the meaning of the term "binding partner."

As used herein, the term "interacts specifically" or "specific interaction," when used in reference to a chimeric pro-caspase, means that the chimeric pro-caspase associates directly or indirectly with its binding partner with a dissociation constant of at least about $1 \times 10^{-6}$, generally at least about $1 \times 10^{-7}$, usually at least about $1 \times 10^{-8}$, and particularly at least about $1 \times 10^{-9}$ or $1 \times 10^{-10}$ or less, to form an oligomeric complex. The chimeric pro-caspase can interact specifically with another chimeric pro-caspase to form a homo-oligomer, or with molecule other than an identical chimeric pro-caspase to form a hetero-oligomer, and the interaction can be a direct interaction of the binding partners or can be mediated by an agent that induces oligomerization. In general, the specific interaction of the binding partners is stable under physiological conditions, including, for example, conditions that occur in a living individual such as a human or other vertebrate, or conditions generally used for culturing an organism such as a bacterium or yeast or cells of an organism such as mammalian cells or other cells from a vertebrate or invertebrate organism. Various well known methods can be used to determine whether a chimeric pro-caspase interacts specifically with its binding partner to form an oligomer, including, for example, equilibrium dialysis, surface plasmon resonance, and the like.

A chimeric pro-caspase contains a pro-caspase domain and an oligomerizing domain. The pro-caspase domain of a chimeric pro-caspase can be a pro-caspase polypeptide such as a pro-caspase form of an initiator caspase, for example, pro-caspase-8 or pro-caspase-1, or a peptide portion of a pro-caspase having caspase activity potential (see, for example, Thornberry and Lazebnik, supra, 1998; Salvesen and Dixit, supra, 1997; Cohen, supra, 1997). As used herein, the term "peptide portion," when used in reference to a pro-caspase, means an amino acid sequence of the pro-caspase that is less than the entire pro-caspase amino acid sequence. Such a peptide portion of a pro-caspase can lack one or a few amino acids from the N-terminus of the naturally occurring pro-caspase, and can lack all or part of the prodomain. In general, a peptide portion of a pro-caspase useful in a chimeric pro-caspase includes most or all of the amino acid sequence of the C-terminus of the pro-caspase, including the portion that is cleaved to produce the small (p10) and large (p18) protease subunits, which confer caspase activity (see FIG. 1).

The oligomerizing domain provides a means through which a chimeric pro-caspase oligomerizes with its binding partner. Depending on the oligomerizing domain utilized, oligomerization can be inducible or can occur spontaneously. Where an oligomerizing domain provides for inducible oligomerization, the association of the chimeric pro-caspase with its binding partner is mediated by an agent that induces oligomerization. As used herein, the term "agent that induces oligomerization" means a molecule that is required for a chimeric pro-caspase to oligomerize with its binding partner. An agent that induces oligomerization can act in various ways. For example, the agent can bind to an oligomerizing domain, resulting in a conformational change in the oligomerizing domain such that it can directly interact with its binding partner. Such an agent acts similarly to a cofactor that, upon binding an enzyme, produces a conformational state suitable for substrate binding by the enzyme.

An agent that induces oligomerization also can act by mediating binding of the chimeric pro-caspase to its binding partner. Such an agent can be, for example, an antibody, which reacts specifically with an oligomerizing domain comprising an epitope for the antibody. An antibody generally can be useful to induce oligomerization of two identical chimeric pro-caspases by binding to an identical epitope in each oligomerizing domain of the chimeric pro-caspases, thereby inducing oligomerization. In addition, a bifunctional antibody can be used to induce oligomerization of a chimeric pro-caspase and a binding partner other than an identical chimeric pro-caspase, wherein one arm of the bivalent antibody reacts specifically with an epitope on the oligomerizing domain of the chimeric pro-caspase and the second arm of the antibody reacts specifically with an epitope on the binding partner, thereby inducing oligomerization.

An agent that induces oligomerization of a chimeric pro-caspase also can be a small chemical molecule, which can mediate the association of oligomerizing domains that specifically interact with the agent. Such molecules, referred to as "dimerizing agents" or "dimerizers," are exemplified by natural and synthetic bivalent chemical compounds such as cyclosporin, rampamycin, coumermycin, FK506, AP1510 and AP1903, which bind to and induce dimerization of the human FKBP12 protein (also called "FK506 binding protein" or "FKBP;" see, for example, Amara et al., *Proc. Natl. Acad. Sci. USA* 94:10618–10623 (1997); Clackson et al., *Proc. Natl. Acad. Sci., USA* 95:10437–10442 (1998); Spencer, *Trends Genet,* 12:181–187 (1996), each of which is incorporated herein by reference). Thus, chimeric pro-caspases can be constructed having an oligomerizing domain based on the FKBP polypeptide, or an FK506 binding domain of FKBP, and can be induced to oligomerize by contacting them with a dimerizing agent. An advantage of such chimeric pro-caspases is that they can be present in a cell, without activating apoptosis in the cell, and the cell can be contacted, when desired, with a membrane permeable dimerizing agent, thereby inducing oligomerization of the chimeric pro-caspase, activating its caspase activity, and inducing apoptosis in the cell.

An oligomerizing domain also can provide for spontaneous oligomerization of a chimeric pro-caspase. As used herein, the term "spontaneous," when used in reference to the oligomerization of a chimeric pro-caspase, means that the chimeric pro-caspase interacts specifically with its binding partner upon attaining the appropriate proximity with the binding partner. As such, no exogenous agent is required for oligomerization to occur. Oligomerizing domains that provide for spontaneous oligomerization can be derived from polypeptides that interact specifically with cellular proteins. For example, an oligomerizing domain can be derived from cellular Raf protein, which interacts specifically with a Ras cellular protein. Ras transmits its growth signal, in part, by aggregating with the Raf kinase (Luo et al., *Nature* 383:178–181 (1996), which is incorporated herein by reference). As such, a chimeric pro-caspase comprising an oligomerizing domain based on the Ras-associating domain of Raf can be provided to a cancer cell, where it can interact specifically with activated Ras, thereby inducing oligomerization of the chimeric pro-caspase and activating its caspase activity and apoptosis in the cancer cells.

Similarly, guanine nucleotide exchange factors (GEF), which convert inactive Ras-GDP to activated Ras-GTP, also can interact specifically with Ras in a cell. Thus, as for Raf, the Ras associating domain of a GEF can be used as an oligomerizing domain of a chimeric pro-caspase of the invention. GEFs are well known in the art and include, for example, Sos1, Sos2 and C3G, which are expressed in various mammalian cells, and Cdc25$^{Mm}$ and Vav, which are expressed specifically in brain cells and in hematopoietic cells, respectively (see, for example, U.S. Pat. No. 5,776,689, which is incorporated herein by reference). The ability to construct chimeric pro-caspases having oligomerizing domains that are active only in one or few specific cell types provides an additional means to restrict caspase activity and, therefore, apoptosis to the desired cells.

A chimeric pro-caspase can contain one or more domains in addition to the pro-caspase domain and the oligomerizing domain. For example, a chimeric pro-capase can contain a protein transduction domain such as the human immunodeficiency virus TAT protein trasduction domain (Schwarze et al., *Science* 285:1569–1572 (1999), which is incorporated herein by reference). Transduction of polypeptides containing the HIV TAT protein transduction domain in vitro is rapid, occurs in a concentration dependent manner, and does not appear to be dependent on any particular cellular receptors or transporters (Derossi et al., *J. Biol. Chem.,* 271:18188 (1996)). Systemic administration of polypeptides containing the protein transduction domain in vivo resulted in delivery of the polypeptides to all tissues, including brain, without compromising the integrity of the blood brain barrier (Schwarze et al., supra, 1999). As such, a chimeric pro-caspase comprising a protein transduction domain is particularly useful when the chimeric pro-caspase is to be administered directly to a cell.

A chimeric pro-caspase also can contain a cell compartmentalization domain, for example, a plasma membrane localization domain, a nuclear localization signal, a mitochondrial membrane localization signal, an endoplasmic reticulum localization signal, or the like (see, for example, Hancock et al., *EMBO J.* 10:4033–4039 (1991); Buss et al., *Mol. Cell. Biol.* 8:3960–3963 (1988), each of which is incorporated herein by reference; see, also, U.S. Pat. No. 5,776,689). Such a domain can be useful to target the chimeric pro-caspase to a particular compartment in the cell, particularly the compartment in which its binding partner is present For example, activated Ras generally is associated with the inner surface of the plasma membrane. Thus, a chimeric pro-caspase containing an oligomerizing domain based on a Ras-associating Raf domain can further comprise a plasma membrane localization domain, thereby localizing the chimeric pro-caspase to the site of Ras in the cell.

Where the chimeric pro-caspase comprises a polypeptide, it can be constructed using any convenient method. Generally, a polypeptide chimeric pro-caspase, or domains comprising the chimeric pro-caspase, is expressed from a recombinant polynucleotide encoding the chimeric pro-caspase or the domains. However, the chimeric pro-caspase also can be prepared, in whole or in part, from an isolated fragment of a protein containing a domain of interest, for example, a proteolytic fragment comprising a Ras-association domain of a Raf protein. Such an isolated fragment comprising the oligomerizing domain can be chemically linked to a pro-caspase domain, for example, through the use of a crosslinking agent, or by forming a disulfide or other amino acid bridge between the two domains, or, particularly, through a peptide bond between the C-terminus of one domain and the N-terminus of a second domain, and so on depending on the number of domains in the chimeric pro-caspase. One or more domains also can be chemically synthesized using well known methods of peptide synthesis, then linked to the other domain or domains comprising the chimeric pro-caspase. Methods of chemical synthesis can be particularly convenient for preparing oligopeptide domains, such as a protein transduction domain, a cell compartmentalization domain, or a relatively small oligomerizing domain.

The domains of a chimeric pro-caspase have been exemplified generally as polypeptide sequences. However, one or more domains of a chimeric pro-caspase can be, for example, a nucleic acid molecule, a peptidomimetic, an oligosaccharide, a lipoprotein, a glycoprotein, a glycolipid, a small organic molecule, or the like. Such molecules useful as a domain in a chimeric pro-caspase, for example, as an oligomerizing domain, can be prepared based on a known structure or can be identified by screening a library of such molecules. Methods for preparing and screening a combinatorial library of such molecules are well known in the art and include, for example, methods of making and screening a phage display library of peptides, which can be constrained peptides (see, for example, U.S. Pat. Nos. 5,622,699; 5,206,347; Scott and Smith, *Science* 249:386–390 (1992); Markland et al., *Gene* 109:13–19(1991), each of which is incorporated herein by reference); a peptide library (U.S. Pat. No. 5,264,563, which is incorporated herein by reference); a peptidomimetic library (Blondelle et al., supra, 1995); a nucleic acid library (O'Connell et al., supra, 1996; Tuerk and Gold, supra, 1990; Gold et al., supra, 1995, each of which is incorporated herein by reference); an oligosaccharide library (York et al., *Carb. Res.,* 285:99–128, (1996); Liang et al., *Science,* 274:1520–1522, (1996); Ding et al., *Adv. Expt. Med. Biol.,* 376:261–269, (1995),each of which is incorporated herein by reference); a lipoprotein library (de Kruif et al., *FEBS Lett.,* 399:232–236, (1996), which is incorporated herein by reference); a glycoprotein or glycolipid library (Karaoglu et al., *J. Cell Biol.,* 130:567–577 (1995), which is incorporated herein by reference); or a chemical library containing, for example, drugs or other pharmaceutical agents (Gordon et al., *J. Med. Chem.,* 37:1385–1401 (1994); Ecker and Crooke, *Bio/Technology,* 13:351–360 (1995), each of which is incorporated herein by reference). Domains comprised of nucleic acid molecules can be particularly useful, for example, as oligomerizing domains, since nucleic acid molecules having binding specificity for cellular targets, including cellular polypeptides, exist naturally, and because synthetic molecules having such specificity can be readily prepared and identified (see, for example, U.S. Pat. No. 5,750,342, which is incorporated herein by reference). Such domains can be engineered into the chimeric pro-caspase using, for example, a chemical linking method specific for the particular domains.

The present invention also provides antibodies that specifically react with a chimeric pro-caspase. As used herein, the term "antibody" is used in its broadest sense to include polyclonal and monoclonal antibodies, as well as antigen binding fragments of such antibodies. An antibody of the invention, or an antigen binding fragment thereof, is characterized by having specific binding activity for a chimeric pro-caspase, but not for the isolated domains comprising the chimeric pro-caspase or for a naturally occurring polypeptide from which the domain was derived. For example, an antibody that reacts specifically with a chimeric pro-caspase comprising a pro-caspase-8 domain and a Ras-associating Raf domain does not substantially react with an isolated pro-caspase-8 or with an isolated Raf polypeptide.

The term "reacts specifically" or "specific binding activity," when used in reference to an antibody of the invention and a chimeric pro-caspase, means that an interaction of the antibody and chimeric pro-caspase has a dissociation constant of at least about $1 \times 10^{-6}$, generally at least about $1 \times 10^{-7}$, usually at least about $1 \times 10^{-8}$, and particularly at least about $1 \times 10^{-9}$ or $1 \times 10^{-10}$ or less. As such, Fab, F(ab')$_2$, Fd and Fv fragments of an antibody of the invention, which retain specific binding activity for the chimeric pro-caspase, are included within the definition of an antibody. For purposes of the present invention, an antibody that reacts specifically with a chimeric pro-caspase is considered to not substantially react with an isolated domain of the chimeric pro-caspase or a polypeptide from which the domain is derived if the antibody has at least a two-fold greater binding affinity, generally at least a five-fold greater binding affinity, and particularly at least a ten-fold greater binding affinity for the chimeric pro-caspase as compared to the isolated domain or the polypeptide from which the domain was derived.

The term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., *Science* 246:1275–1281 (1989), which is incorporated herein by reference). These and other methods of making, for example, chimeric, humanized, CDR-grafted, single chain, and bifunctional antibodies are well known to those skilled in the art (Winter and Harris, *Immunol. Today* 14:243–246 (1993); Ward et al., *Nature* 341:544–546 (1989); Harlow and Lane, *Antibodies: A laboratory manual* (Cold Spring Harbor Laboratory Press, 1988); Hilyard et al., *Protein Engineering: A practical approach* (IRL Press 1992); Borrabeck, *Antibody Engineering,* 2d ed. (Oxford University Press 1995); each of which is incorporated herein by reference).

Antibodies that react specifically with a chimeric pro-caspase can be raised using the chimeric pro-caspase or a peptide portion thereof as an immunogen. A non-immunogenic peptide portion of a chimeric pro-caspase can be made immunogenic by coupling the hapten to a carrier molecule such bovine serum albumin (BSA) or keyhole limpet hemocyanin (KLH), or by expressing the peptide portion as a fusion protein. Various other carrier molecules and methods for coupling a hapten to a carrier molecule are well known in the art (see, for example, by Harlow and Lane, supra, 1988).

The antibodies of the invention are useful for identifying the presence of a chimeric pro-caspase in a sample, which can be, for example, a reaction mixture in which the chimeric pro-caspase was prepared, or an extract from a cell in which the chimeric pro-caspase was expressed from an encoding polynucleotide. Such antibodies also can be used to purify a chimeric pro-caspase from a sample. For example, the antibodies can be bound to a solid matrix such as a chromatography matrix, then the sample can be contacted with the antibodies. Following washing of the matrix to remove unbound material, the chimeric pro-caspases can be released from the antibodies and obtained in a substantially isolated form. Methods for attaching antibodies to solid matrices and for eluting bound antigens from such antibodies are well known in the art (see Harlow and Lane, supra, 1988).

The antibodies of the invention also can be used in immunological assays, for example, to identify a cell containing a chimeric pro-caspase. As disclosed herein, a chimeric pro-caspase can be introduced into a cell directly, or can be expressed in the cell from a polynucleotide encoding the chimeric pro-caspase. Upon providing cells in a subject with a chimeric pro-caspase using the methods disclosed herein, a tissue sample can be obtained from a subject, for example, by a biopsy procedure, and can be prepared for an immunoassay procedure such as a radioimmunoassay (RIA) or an enzyme linked immunosorbent assay (ELISA), or can be examined by microscopy using an immunohistological method.

If desired, a kit incorporating an antibody of the invention can be prepared. Such a kit can contain, in addition to the anti-chimeric pro-caspase antibody, a reaction cocktail that provides the proper conditions for performing an immunological assay, control samples that contain known amounts of the chimeric pro-caspase and, if desired, a second antibody specific for the anti-chimeric pro-caspase antibody. Such an assay also can include a simple method for detecting the presence or amount of a chimeric pro-caspase in a sample. Accordingly, the invention provides such kits, which contain an anti-chimeric pro-caspase antibody.

Methods for raising polyclonal antibodies, for example, in a rabbit, goat, mouse or other mammal, are well known in the art. In addition, monoclonal antibodies can be obtained using methods that are well known and routine in the art (Harlow and Lane, supra, 1988). For example, spleen cells from a mouse immunized with a chimeric pro-caspase or an epitopic fragment thereof can be fused to an appropriate myeloma cell line such as SP/02 myeloma cells to produce hybridoma cells. Cloned hybridoma cell lines can be screened using labeled chimeric pro-caspase to identify clones that secrete anti-chimeric pro-caspase monoclonal antibodies, and hybridomas expressing antibodies having a desirable specificity and affinity can be isolated and utilized as a continuous source of the antibodies. Such antibodies are useful, for example, for preparing standardized kits as described above. A recombinant phage that expresses, for example, a single chain anti-chimeric pro-caspase also provides an antibody that can used for preparing standardized kits.

A chimeric pro-caspase or a polypeptide such as anti-chimeric pro-caspase antibody can be labeled so as to be detectable using methods well known in the art (Hermanson, "Bioconjugate Techniques" (Academic Press 1996), which is incorporated herein by reference; Harlow and Lane, supra, 1988). For example, a chimeric pro-caspase or an antibody can be labeled with various detectable moieties including a radiolabel, an enzyme, biotin or a fluorochrome. Reagents for labeling an anti-chimeric pro-caspase antibody, for example, can be included in a kit containing the antibody or can be purchased separately from a commercial source.

The invention also provides polynucleotides encoding a polypeptide chimeric pro-caspase or a polypeptide portion of a chimeric pro-caspase. As used herein, the term "polynucleotide" is used in its broadest sense to mean two or more nucleotides or nucleotide analogs linked by a covalent bond. The polynucleotide can be single stranded or double stranded, and can be DNA, RNA or a DNA/RNA hybrid. A polynucleotide of the invention generally encodes portions of at least two domains of a chimeric pro-caspase, or portions of the domains. The polynucleotide is constructed such that the domain comprising the chimeric pro-caspase generally are linked in frame, although they need not be contiguous and can separated by a spacer or other amino acid sequence, which, if desired, can have a desirable function such as acting as a cleavage site for a protease. A polynucleotide that encodes all or a portion of a chimeric pro-caspase is referred to as an "encoding polynucleotide."

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can comprise nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220–5234 (1994); Jellinek et al., *Biochemistry* 34:11363–11372 (1995); Pagratis et al., *Nature Biotechnol.* 15:68–73 (1997), each of which is incorporated herein by reference).

The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977–986 (1994); Ecker and Crooke, *Bio Technology* 13:351360 (1995), each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (see Jellinek et al., supra, 1995).

The term "oligonucleotide" also is used herein to mean two or more nucleotides or nucleotide analogs linked by a covalent bond, although those in the art will recognize that oligonucleotides generally are less than about fifty nucleotides in length and, therefore, are a subset of "polynucleotides." Oligonucleotides of the invention generally are at least about 8 nucleotides in length, usually at least about 12 nucleotides in length, and particularly at least about 15 or 20 nucleotides in length, such that they can specifically hybridize to a polynucleotide encoding a chimeric pro-caspase under conditions generally used for hybridization analysis.

The oligonucleotides of the invention are characterized, in part, in that they hybridize to a polynucleotide encoding a chimeric pro-caspase, but not to a polynucleotide encoding an individual domain of the chimeric pro-caspase or a polypeptide from which the domain was derived. As such, the oligonucleotides can be used, for example, for Southern blot or northern blot analyses, in which case the oligonucleotide can be detectably labeled with a moiety such as a radionuclide or a fluorescent, luminescent or chemiluminescent molecule or biotin or the like; or for PCR analysis, in which case the oligonucleotides comprise primers. The oligonucleotides of the invention are useful, for example, for identifying a cell containing a polynucleotide encoding a chimeric pro-caspase, including a cell expressing such a polynucleotide.

The invention also provides vectors containing a polynucleotide or oligonucleotide of the invention, and host cells containing such vectors. The vector can be a cloning vector or an expression vector, depending on the purpose for which the polynucleotide is contained in the vector. For example, the vector can be a cloning vector where polynucleotides encoding chimeric pro-caspases having diverse oligomerizing domains have been constructed. The cloning vectors can be used to produce a library of such polynucleotides, which then can be screened to identify polynucleotides having a desired sequence.

The vector also can be an expression vector, which contains, in addition to an encoding polynucleotide, regulatory elements useful for expressing the encoded polypeptide in a particular cell. An expression vector can contain the expression elements necessary to achieve, for example, sustained transcription of the encoding polynucleotide, or the regulatory elements also can be operably linked to the polynucleotide prior to its being cloned into the vector. The term "operably linked," when used in reference to a regulatory element, means that the regulatory element is positioned with respect to a polynucleotide encoding a chimeric pro-caspase, or a portion thereof, such that the regulatory element effects transcription or translation of the coding sequence in substantially the same manner as it does when the regulatory element is present in its natural position in a genome.

An expression vector (or the polynucleotide) generally contains or encodes a promoter sequence, which can provide constitutive or, if desired, inducible expression of the encoding polynucleotide, a poly-A recognition sequence, and a ribosome recognition site or internal ribosome entry site, and can contain other regulatory elements such as an enhancer, which can be tissue specific. The vector also contains elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, *Meth. Enzymol.,* Vol. 185, Goeddel, ed. (Academic Press, Inc., 1990); Jolly, *Canc. Gene Ther.* 1:51–64 (1994); Flotte, *J. Bioenerg. Biomemb.* 25:37–42 (1993); Kirshenbaum et al., *J. Clin. Invest.* 92:381–387 (1993), each of which is incorporated herein by reference).

Viral expression vectors can be particularly useful for introducing a polynucleotide encoding a chimeric pro-caspase into a cell, since viral vectors can infect host cells with relatively high efficiency and can infect specific cell types. For example, a polynucleotide of the invention can be cloned into a baculovirus vector, which then can be used to infect an insect host cell, thereby providing a means to produce large amounts of the encoded chimeric polypeptide. In addition, the viral vector can be derived from a virus that infects vertebrate host cells, particularly mammalian host cells. Viral vectors can be particularly useful for introducing a polynucleotide encoding a chimeric pro-caspase into a mammalian cell, wherein, upon expression of the chimeric pro-caspase, oligomerization can occur, thereby activating the caspase activity and inducing apoptosis in the cell. Viral vectors have been developed for use in mammalian systems and include, for example, retroviral vectors, other lentivirus vectors such as those based on the human immunodeficiency virus (HIV), adenovirus vectors, adeno-associated virus vectors, herpesvirus vectors, vaccinia virus vectors, and the like (see Miller and Rosman, *BioTechniques* 7:980–990 (1992); Anderson et al., *Nature* 392:25–30 Suppl. (1998); Verma and Somia, *Nature* 389:239–242 (1997); Wilson, *New Engl. J. Med.* 334:1185–1187 (1996), each of which is incorporated herein by reference).

When retroviruses, for example, are used for gene transfer, replication competent retroviruses theoretically can develop due to recombination of retroviral vector and viral gene sequences in the packaging cell line utilized to produce the retroviral vector. Packaging cell lines in which the production of replication competent virus by recombination has been reduced or eliminated can be used to minimize the likelihood that a replication competent retrovirus will be produced. All retroviral vector supernatants used to infect cells are screened for replication competent virus by standard assays such as PCR and reverse transcriptase assays. Retroviral vectors allow for integration of a heterologous gene into a host cell genome, which allows for the gene to be passed to daughter cells following cell division.

A polynucleotide, which can be contained in a vector, can be introduced into a cell by any of a variety of methods known in the art (Sambrook et al., "Molecular Cloning: A laboratory manual" (Cold Spring Harbor Laboratory Press 1989); Ausubel et al., "Current Protocols in Molecular Biology" (John Wiley and Sons, Baltimore, Md. 1994), each of which is incorporated herein by reference). Such methods include, for example, transfection, lipofection, microinjection, electroporation and infection with recombinant vectors, and can include the use of liposomes, microemulsions or the like, which can facilitate introduction of the polynucleotide into the cell and can protect the polynucleotide from degradation prior to its introduction into the cell.

Introduction of a polynucleotide into a cell by infection with a viral vector is particularly advantageous in that it can efficiently introduce the nucleic acid molecule into a cell ex vivo or in vivo (see, for example, U.S. Pat. No. 5,399,346, which is incorporated herein by reference). Moreover, viruses are very specialized and typically infect and propagate in specific cell types. Thus, their natural specificity can be used to target the nucleic acid molecule contained in the vector to specific cell types. As such, a vector based on an HIV can be used to infect T cells, a vector based on an adenovirus can be used, for example, to infect respiratory epithelial cells, a vector based on a herpesvirus can be used to infect neuronal cells, and the like. Other vectors, such as adeno-associated viruses can have greater host cell range and, therefore, can be used to infect various cell types, although viral or non-viral vectors also can be modified with specific receptors or ligands to alter target specificity through receptor mediated events.

As disclosed herein, oligomerization of pro-caspases induced proteolytic generation of mature caspase subunits and activated their cell death activity (see, also, Yang et al., supra, 1998a, 1998b). Deletion of the protein interaction motif, DED ("death effector domain"), from pro-caspase-8 greatly suppressed its apoptotic activity (see Example I). Cell death activity was restored by oligomerizing pro-caspase-8 protease domains using two heterologous inducible oligomerization systems. Induced oligomerization also activated the apoptotic activity of pro-caspase-1, but not pro-caspase-3. In vitro, oligomerization resulted in pro-caspase processing to form the mature caspase subunits; this processing required the intrinsic caspase activity of zymogens and proceeded via a previously unknown order of cleavage events (Example I).

Two inducible oligomerization systems were used to demonstrate that oligomerization activates pro-caspase processing, thereby activating caspase activity. Pro-caspase-8 products obtained in a cell-free processing system indicated that the prodomain is first separated from the protease domain, followed by the separation of the two protease subunits (see Example I). This order of cleavages is distinct from that observed when pro-caspase-8 was used as a substrate for active DISC (Medema et al., supra, 1997). Thus, pro-caspase processing by oligomerization occurs through a distinct mechanism from that involved in processing of a pro-caspase by a mature caspase as occurs in other steps of the cascade.

Figure 3A:
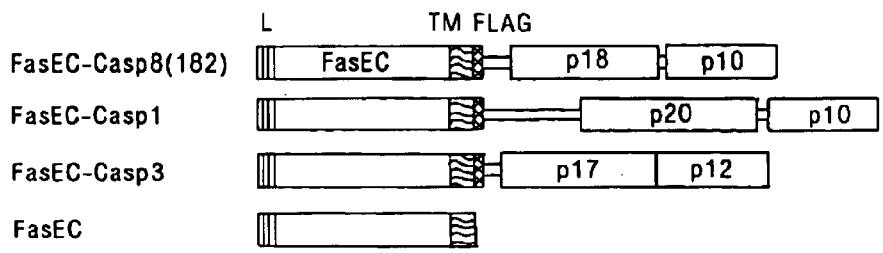
FIG. 3A to 3C show apoptotic activity of pro-caspase fusions with the Fas extracellular domain.
Figure 3B:
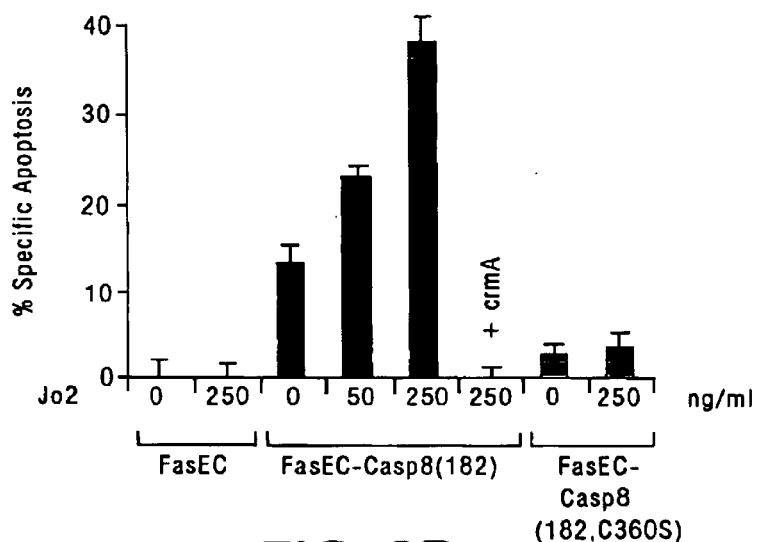
Figure 5A:
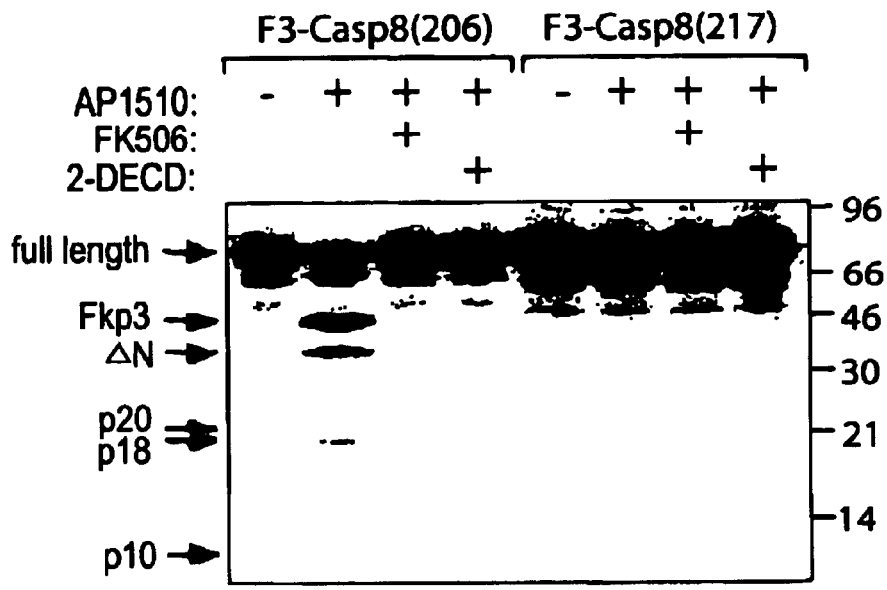
FIGS. 5A and 5B show pro-caspase processing in a cell-free system.

Oligomerization-induced activation likely reflects the in vivo situation for pro-caspase-8, which is known to occur at caspase sites (Medema et al., supra, 1997). Oligomerization-induced processing was inhibited by the caspase inhibitor, Z-DEVD (see Example I; FIG. 5A), and was abrogated by deletion of the recognition site at amino acid 216 (FIG. 4A, FIG. 5A). In addition, the processed products correspond to the intermediates detected in cells undergoing Fas-induced apoptosis (Medema et al., supra, 1997). Furthermore, by making a FasEC-caspase-8 fusion, the intervening protein interaction motifs for the in vivo Fas-FADD-caspase-8 connection were by-passed. FasEC-caspase-8 killed cells in a Jo2-dependent manner, strikingly similar to Fas-mediated cell death (FIG. 3B). Therefore, the in vivo function of many proteins in the Fas receptor complex is likely to facilitate and regulate oligomerization of pro-caspase-8.

Oligomerization of pro-caspases can be a general mechanism in initiating caspase cascades. Caspases have been divided into three major groups—a caspase-8-like group, a caspase-1-like group, and a caspase-3-like group—based on their substrate specificities (Thornberry et al., supra, 1997). As disclosed herein, oligomerization induced the activation of pro-caspase-8 and pro-caspase-1 (see Example I). A caspase-3-like protease, caspase-2 (Ich-1), binds to the death adaptor RAIDD via its prodomain and is recruited to TNF receptor-1 (Duan and Dixit, Nature 385:86–89 (1997)). Membrane recruitment and oligomerization of pro-caspase-2 then can lead to autoproteolytic activation in a fashion similar to that found for pro-caspase-8. In comparison, induced oligomerization of pro-caspase-3 did not enhance its cell death activity. These results indicate that prodomain structure, rather than substrate specificity, can determine the ability of a pro-caspase to be activated by oligomerization. Furthermore, this difference between pro-caspase-8 and pro-caspase-1 as compared to pro-caspase-3 reinforces the conceptual division of initiator and executioner caspases, and indicates that oligomerization-induced activation is a property of the initiator caspases.

Controlling the oligomerization state of pro-caspases can be a critical regulatory event in the cellular decision for life or death. Specific adaptor proteins that interact with the prodomains of various pro-caspases may allow distinct apoptotic stimuli to engage the cell death machinery by inducing pro-caspase oligomerization. A logical step in inducing pro-caspase oligomerization is to bring them near membranes, thus reducing their movement from three dimensions to two dimensions and increasing their local concentration. A recent study showed that pro-caspase-8 can be recruited to the endoplasmic reticulum (ER) membrane through an ER protein, p28 Bap31 (Ng et al., J. Cell Biol. 139:327–338 (1997), which is incorporated herein by reference). Cell death effectors such as CED-4, Bcl-2, and cytochrome c may exert their effects through regulating oligomerization of pro-caspases. The Caenorhabditis elegans death effector CED-4 and its mammalian homolog Apaf-1 interact with the zymogen form of CED-3 and caspase-9, respectively (Hengartner, Nature 388:714–715 (1997); Li et al., Cell 91 :479–489 (1997)). CED-4 also associates with the cell death inhibitor CED-9, while Apaf-1 associates with the cell death initiator cytochrome c (Hengartner, supra, 1997). It is likely that additional regulatory strategies also control the activity of caspases.

Oligomerization-induced activation of pro-caspases is reminiscent of the activation of receptor tyrosine kinases. Oligomerization of receptor tyrosine kinases leads to intermolecular cross-phosphorylation, which can increase their kinase activity and enhance their interaction with cellular proteins (Ullrich and Schlessinger. Cell 61:203–212 (1990)). In a similar manner, autoproteolytic processing of pro-caspases produces mature caspases that possess greater enzymatic activity. Oligomerization-induced autoproteolysis is an established mechanism in activating the complement protease cascade. As disclosed herein, a similar mechanism is used to initiate an intracellular protease cascade for programmed cell death, and provides an additional example of oligomerization in activating signal transduction pathways.

The discovery that cell growth and cell death are controlled by similar mechanisms provides a means by which growth signals can be turned into death signals (and vice versa) by straight-forward manipulations. Accordingly, the present invention provides a method of inducing apoptosis in a cell by providing a chimeric pro-caspase in the cell, whereby the chimeric pro-caspase forms an oligomer in the cell, thereby activating caspase activity of the chimeric pro-caspase and inducing apoptosis in the cell. Such a method can be used for inducing apoptosis in a cell in vitro, or for inducing apoptosis in a cell in vivo.

As used herein, the term "providing a chimeric pro-caspase in a cell" means either that a chimeric pro-caspase is introduced into the cell or that a polynucleotide encoding a chimeric pro-caspase is introduced into the cell, after which the encoded chimeric pro-caspase is expressed in the cell. Well known methods can be used for determining that a chimeric pro-caspase is provided in a cell. Where the chimeric pro-caspase is introduced directly into the cells or is expressed from a polynucleotide introduced into the cells, its presence in the cell can be detected directly using an antibody that reacts specifically with the chimeric pro-caspase. For example, a cell extract can be prepared from the cells and a western blot analysis or an immunoassay such as an RIA or ELISA can be performed.

If desired, the chimeric pro-caspase can comprise a detectable marker such as a FLAG epitope, thus allowing the use of an anti-FLAG antibody to detect the presence of the chimeric pro-caspase in the cell (see, for example, Hopp et al., *BioTechnology* 6:1204 (1988); U.S. Pat. No. 5,011,912, each of which is incorporated herein by reference). Other detectable markers such as a c-myc epitope, which can be detected using an antibody specific for the epitope; a polyhistidine sequence, which can be detected using a divalent cation such as nickel ion, cobalt ion, or the like; biotin, which can be detected using streptavidin or avidin; glutathione S-transferase, which can be detected using glutathione; or the like also can be used to identify the presence of a chimeric pro-caspase in a cell. Such markers can provide the additional advantage that they can be used as a tag to facilitate isolation of the pro-caspase, for example, where it is desired to obtain a relatively purified chimeric pro-caspase preparation.

Where the chimeric pro-caspase is expressed from a polynucleotide, which is introduced into the cells, the presence of the chimeric pro-caspase in the cell can be detected indirectly by performing northern blot analysis using an oligonucleotide probe that hybridizes specifically with the encoding polynucleotide and detecting the presence of the an mRNA encoded by the introduced polynucleotide. An oligonucleotide primer also can be used and PCR can be performed to detect the presence of the introduced polynucleotide, or of mRNA expressed from the polynucleotide. If desired, the polynucleotide encoding the chimeric pro-caspase can further comprise a nucleotide sequence encoding a detectable marker such as green fluorescent protein (see FIG. 6), β-galactosidase, luciferase, or the like, thus facilitating detection of the expressed chimeric pro-caspase. Such detectable markers can be particularly useful because cells containing the chimeric pro-caspase can be detected visually, and because such markers can facilitate high throughput analysis of cells, for example, where it is desired to use a method such as fluorescence activated cell sorting to separate cells containing the chimeric pro-caspase from those lacking it.

Although chimeric pro-caspases generally are large polypeptides, which do not readily traverse a cell membrane, various methods are known for introducing a polypeptide into a cell. The selection of a method for introducing the chimeric pro-caspase into a cell will depend, in part, on the characteristics of the target cell, into which the chimeric pro-caspase is to be provided. For example, where the target cells, or a few cell types including the target cells, express a receptor, which, upon binding a particular peptide ligand, is internalized into the cell, the chimeric pro-caspase can include a domain corresponding to the peptide ligand. Upon binding to the receptor, the chimeric pro-caspase is translocated into the cell by receptor-mediated endocytosis. A chimeric pro-caspase also can be contained in a liposome or formulated in a lipid complex, which can facilitate entry of the chimeric pro-caspase into the cell. A chimeric pro-caspase also can be introduced into a cell by engineering the chimeric pro-capase to contain a protein transduction domain such as the human immunodeficiency virus TAT protein transduction domain, which facilitates translocation of the chimeric pro-caspase into the cell (see Schwarze et al., supra, 1997).

A method of the invention also can be performed by introducing a polynucleotide encoding the chimeric pro-caspase into the cell, and expressing the encoded chimeric pro-caspase. The encoding polynucleotide, which can be contained in an expression vector, for example, a viral expression vector, can be contacted directly with the cells, or can be contained in a liposome or formulated in a lipid complex, microemulsion, or the like, which can facilitate introduction into the cell. Upon expression, the chimeric pro-caspase can oligomerize spontaneously or can be induced to oligomerize, thereby activating caspase activity of the chimeric pro-caspase and inducing apoptosis in the cell.

A method of the invention can be useful for ridding a mixed population of cells of one or more undesirable populations of cells. For example, the method can be used to selectively kill a undesirable population of cells in culture that threaten to overgrow a desirable population of cells. The chimeric pro-caspases can be provided selectively to the undesirable population of cells based, for example, on the use of viral vector that infects the undesirable, but not the desirable population of cells, or on a higher transfection efficiency of the undesirable cells as compared to the desirable cells, or some other distinguishing characteristic of the undesirable cells such that the chimeric pro-caspase or an encoding polynucleotide preferentially is taken up by the undesirable cells. Alternatively, the chimeric pro-caspases can be designed to oligomerize selectively in the undesirable cells based, for example, on the presence of an oligomerizing domain in the chimeric pro-caspase that spontaneously oligomerizes with a polypeptide that is expressed only, or at a higher level, in the undesirable cells.

Where the cells in which apoptosis is to be induced are obtained from or are present in a subject suffering from a pathologic condition, a method of the invention provides a means to treat the subject. Accordingly, the present invention provides a method of reducing the severity of a pathologic condition in a subject, by providing cells involved in the pathologic condition in the subject with a chimeric pro-caspase, whereby the chimeric pro-caspase can oligomerize in the cell, thereby activating caspase activity of the chimeric pro-caspase, inducing apoptosis in the cells, and reducing the severity of the pathologic condition in the subject.

The term "pathologic condition" is used herein to refer to any disorder that is characterized, at least in part, by the presence of cells that are deleterious to the health of a subject. The pathologic condition can be, for example, a cell proliferative disorder that is characterized, in part, by a loss of growth regulation, which can be due to an undesirably high level of cell proliferation or to an undesirably low level of programmed cell death, or can be characterized by cells that do not exhibit a loss of growth control, but instead exhibit a dysregulation of cell function that contributes to the pathologic condition. Reference herein to cells as being "associated with" or "involved in" a pathologic conditions means those cells that primarily contribute to the signs and symptoms of the pathologic condition and in which it is desired to induce apoptosis. Generally, the cells associated with the pathologic condition correspond to cells that normally are present in the subject. However, the cells can be, for example, transplanted cells that are involved in a graft-versus-host response and, therefore, are involved in a pathologic condition.

The use of a chimeric pro-caspase for treating a pathologic condition such as cancer provides a significant therapeutic advantage over conventional cancer therapies, including surgery, chemotherapy, and radiation therapy, because the chimeric pro-caspases can be effective against disseminated disease and can produce minimal toxic side effects toward normal tissue. Current cancer therapies approaches this goal empirically and indirectly. Surgery can be an effective treatment, in that it can remove a tumor in bulk. However, surgery is only effective if the cancer cells have not spread from the primary site. In addition, surgery can produce significant morbidity. Radiation therapy and chemotherapy can be used to treat more disseminated cancers damage, but generally act by killing rapidly dividing cells, which includes both cancerous cells and normal cells. As a result, these therapies have deleterious effects on rapidly renewing tissues such as the bone marrow and gastrointestinal tract, which often limits the amount of treatment that can be administered. As disclosed herein, chimeric pro-caspases are rationally designed and, therefore, can be engineered, for example, to target a component of a biochemical pathway involved in a cell involved in a pathologic condition, for example, cancer cells. As such, chimeric pro-caspases of the invention provide a more specific therapeutic agent that is less likely to produce significant toxic side effects.

Chimeric pro-caspases also can be more potent therapeutic agents than current treatments because radiation therapy and chemotherapy, for example, depend on damaged cancer cells to respond by initiating programmed cell death. However, cancer cells frequently acquire additional mutations in the damage response circuit and become resistant to treatment. As a result, many types of cancers, particularly in their later stages, become refractory to chemotherapy and radiation therapy. In contrast, chimeric pro-caspases have enzymatic activity that directly induces apoptosis, thus by-passing potential mutations that can otherwise interfere with the induction of programmed cell death. In fact, active caspases can efficiently kill cancer cells even after the cells have become resistant to a chemotherapeutic treatment.

A method of the invention can reduce the severity of a pathologic condition in a subject by inducing apoptosis in cells associated with the pathologic condition in the subject. As used herein, the term "reduce the severity of a pathologic condition" means that particular signs or symptoms associated with the pathologic condition qualitatively or quantitatively are lessened. The signs or symptoms to be monitored will be characteristic of a particular pathologic condition and will be well known to skilled clinician, as will the methods for monitoring the signs and conditions. For example, where the pathologic condition is a malignant neoplasia, the skilled clinician can monitor the size or growth rate of a tumor using diagnostic imaging methods, and can determine that the severity of the condition is reduced by detecting a decreased growth rate or decreased size of the tumor. In addition, the clinician can monitor the level of an enzyme, antigen or other biological product that is prognostic of the status of the condition, for example, prostate specific antigen, carcinoembryonic antigen, or the like, as relevant. The clinician also can identify a reduction in the severity of the condition simply by the treated subject indicating that he or she feels less nausea, or more strength, or just generally feels better. Where the pathologic condition is vascular stenosis, the clinician can determine whether the severity of the condition is reduced by performing an angiogram, by measuring blood flow through the involved blood vessel, by examining the level of fatigue exhibited by the patient following a particular task, or the like. Where the pathologic condition is an autoimmune disease, the clinician can determine the immunoreactivity of the patient's immu-nocytes in an appropriate in vitro immunologic assay, can biopsy the involved tissue and examine the histopathologic or immunohistologic status of the tissue, can examine the mobility of joint involved in the condition or the pain associated therewith, or the like.

The severity of various pathologic conditions can be reduced using a method of the invention. Such pathologic conditions include, for example, malignant neoplasms such as a carcinoma or fibrosarcoma of the breast, prostate, lung, liver, colon, rectum, kidney, stomach, pancreas, ovary, bladder, cervix, uterus, or brain; a glioblastoma; an astrocytoma; or other malignant neoplasm, including metastatic lesions; and benign neoplasms such as benign prostatic hyperplasia, meningioma, hemangioma and angiofibroma. Other pathologic conditions amenable to treatment using a method of the invention include, for example, conditions that are associated with undesirably high levels of angiogenesis such as occurs in diabetic retinopathy, corneal graft neovascularization and neovascular glaucoma, as well as inflammatory conditions such as synovitis, dermatitis and bacterial infection or other infectious conditions, which can be associated with undesirable angiogenesis; endometriosis; arterial stenosis, including, for example, coronary artery stenosis and restenosis, which can occur following an angioplasty procedure; epithelial conditions such as psoriasis; and the formation of hypertrophic scars such as keloids or of vascular adhesions as occur in granulation tissues, including bums, pyogenic granuloma, and the like. In addition, autoimmune diseases such as rheumatoid arthritis, systemic lupus erythematosis, and the like, which are characterized, in part, by the presence in the subject of dysregulated immunocytes, are amenable to treatment using a method of the invention.

A method of the invention can be performed by providing cells of the subject that are involved in the pathologic condition with a chimeric pro-caspase ex vivo, then administering surviving cells to the subject, thereby reducing the severity of the pathologic condition in the subject. Autoimmune diseases, for example, are characterized by the presence in the subject of immunocytes that are dysregulated, in that they do not recognize a normal epitope expressed in a subject, treat the epitope as a foreign antigen, and generate the production of autoantibodies against the antigen and, therefore, against the subject. Such immunocytes, which generally are B cells, are generated from precursor cells, including stem cells and memory cells, which are present in the bone marrow, spleen or lymph nodes or circulate in the blood or lymph fluid of the subject. As such, bone marrow cells and cells from the spleen or lymph nodes, for example, can be obtained from the patient and placed in appropriate cell culture conditions, and can be contacted with chimeric pro-caspases of the invention or with polynucleotides encoding the chimeric pro-caspases as desired.

In such a method, the chimeric pro-caspases are designed such that they oligomerize only in the cells in which apoptosis is to be induced. For example, the autoimmune disease can be characterized, in part, by the expression of antibodies that are reactive against an epitope in the subject. Where the epitope is known, the oligomerizing domain of the chimeric pro-caspase can include the epitope, which further can comprise a protein trasduction domain if the chimeric pro-caspase is to be administered to the cells. Where the antigen is not known, but the antibodies can be isolated, an anti-idiotypic antibody can be prepared and can serve the function of an oligomerizing domain. A goal of using such chimeric pro-caspases is that the deleterious antibodies can induce oligomerization of the chimeric procaspases only in the cells that produce the antibody, thereby specifically killing the cells associated with the pathology, while sparing normal cells. Since the antibodies generally are confined to particular compartments in the antibody producing cells, the chimeric pro-caspase further comprises the appropriate cell compartmentalization domain, thus localizing the chimeric pro-caspase in proximity to the antibodies. Apoptosis of the cells that produce the deleterious antibodies occurs, after which the surviving cells can be reinfused into the patient, thereby reducing the severity of the autoimmune disease.

In treating an autoimmune disease as disclosed above, the cells can be provided with a polynucleotide encoding the chimeric pro-caspase and the polynucleotide can become integrated into the genome of stem cells or other B cell precursor cells of the subject. In such a case, it can be preferable to construct the polynucleotide such that it is operably linked to an expressible regulatory element, for example, a B cell specific regulatory element. Using such a construct, any immunocytes that are newly generated from the stem cells and otherwise would contribute to the pathologic condition are killed upon maturation to the stage in which antibody production occurs, since the antibodies will induce oligomerization of the expressed chimeric pro-caspase.

A similar method can be used to treat virally infected cells such as HIV infected T cells. In such a method, the chimeric pro-caspase is designed to contain an oligomerizing domain that specifically interacts with an HIV polypeptide that is expressed in the virally infected cell, thereby inducing apoptosis in T cells that are infected with HIV. If desired, apoptosis of the T cells containing the chimeric pro-caspase can occur in vitro, after which the surviving cells are administered back into the subject, or the T cells can be reinfused into the subject and apoptosis of the cells can occur in the subject. If desired, the encoding polynucleotide can be operably linked to an HIV regulatory element such that expression of the chimeric pro-caspase occurs in concert with expression of the HIV polypeptide binding partner. Such a method conveniently restricts apoptosis to HIV infected cells that otherwise would produce infective viruses. The encoding polynucleotide also can be cloned into a viral expression vector derived from HIV, thus facilitating infection of T cells, which also are the target cells for HIV infection. Such an HIV viral vector containing the encoding polynucleotide can be particularly useful for an in vivo gene therapy procedure. Thus, a method of the invention can be performed by providing cells of the subject that are involved in the pathologic condition with a chimeric pro-caspase in vivo, whereby the chimeric pro-caspase forms an oligomer in the cells, thereby activating caspase activity of the chimeric pro-caspase, inducing apoptosis in the cells, and reducing the severity of the pathologic condition in the subject.

A chimeric pro-caspase, or a polynucleotide encoding the chimeric pro-caspase, can be administered to the site of the pathologic condition, or by any method that provides the cells associated with the pathologic condition with the chimeric pro-caspase. For administration to a living subject, a chimeric pro-caspase generally is formulated in a pharmaceutical composition suitable for administration to the subject. Thus, the invention further provides pharmaceutical compositions, which contain an agent and a chimeric pro-caspase or a polynucleotide encoding a chimeric pro-caspase in a pharmaceutically acceptable carrier. As such, the chimeric pro-caspases of the invention and the polynucleotides encoding the chimeric pro-caspases are useful as medicaments for treating a subject suffering from a pathological condition.

Pharmaceutically acceptable carriers are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the physico-chemical characteristics of the therapeutic agent, for example, on whether a chimeric pro-caspase polypeptide or a polynucleotide encoding the chimeric pro-caspase is to be administered; and on the route of administration of the composition, which can include, for example, orally or parenterally such as intravenously, and by injection, intubation, or other such method known in the art. The pharmaceutical composition also can contain an agent such as a diagnostic agent, nutritional substance, toxin, or therapeutic agent, for example, a cancer chemotherapeutic agent.

The chimeric pro-caspase or encoding polynucleotide can be incorporated within an encapsulating material such as into an oil-in-water emulsion, a microemulsion, micelle, mixed micelle, liposome, microsphere or other polymer matrix (see, for example, Gregoriadis, *Liposome Technology*, Vol. 1 (CRC Press, Boca Raton, Fla. 1984); Fraley, et al., *Trends Biochem. Sci.*, 6:77 (1981), each of which is incorporated herein by reference). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882, 679; 5,395,619; and 5,225,212, each of which is incorporated herein by reference) are an example of such encapsulating materials particularly useful for preparing a pharmaceutical composition of the invention and for practicing a method of the invention, and other "masked" liposomes similarly can be used, such liposomes extending the time that the therapeutic agent remain in the circulation. Cationic liposomes, for example, also can be modified with specific receptors or ligands (Morishita et al., *J. Clin. Invest.*, 91:2580–2585 (1993), which is incorporated herein by reference). In addition, a nucleic acid molecule can be introduced into a cell using, for example, adenovirus-polylysine DNA complexes (see, for example, Michael et al., *J. Biol. Chem.* 268:6866–6869 (1993), which is incorporated herein by reference).

The route of administration of a pharmaceutical composition of the invention will depend, in part, on the chemical structure of the chimeric pro-caspase. Polypeptides and polynucleotides, for example, are not particularly useful when administered orally because they can be degraded in the digestive tract. However, methods for chemically modifying polypeptides, for example, to render them less susceptible to degradation by endogenous proteases or more absorbable through the alimentary tract arc well known (see, for example, Blondelle et al., supra, 1995; Ecker and Crook, supra, 1995). In addition, the chimeric pro-caspases can be prepared from domains that are identified from libraries of peptides containing D-amino acids; peptidomimetics consisting of organic molecules that mimic the structure of a coagulation factor; or peptoids such as vinylogous peptoids, using the screening methods disclosed herein.

A pharmaceutical composition comprising a chimeric pro-caspase or encoding polynucleotide can be administered to an individual by various routes including, for example, orally or parenterally, such as intravenously, intramuscularly, subcutaneously, intraorbitally, intracapsularly, intraperitoneally, intrarectally, intracisternally or by passive or facilitated absorption through the skin using, for example, a skin patch or transdermal iontophoresis, respectively. Furthermore, the pharmaceutical composition can be administered by injection, intubation, orally or topically, the latter of which can be passive, for example, by direct application of an ointment, or active, for example, using a nasal spray or inhalant, in which case one component of the composition is an appropriate propellant. A pharmaceutical composition also can be administered to the site of a pathologic condition, for example, intravenously or intra-arterially into a blood vessel supplying a tumor.

The total amount of a chimeric pro-caspase or encoding polynucleotide to be administered can be administered to a subject as a single dose, either as a bolus or by infusion over a relatively short period of time, or can be administered using a fractionated treatment protocol, in which multiple doses are administered over a prolonged period of time. One skilled in the art would know that the amount of the pharmaceutical composition to treat a pathologic condition in a subject depends on many factors including the age and general health of the subject as well as the route of administration and the number of treatments to be administered. In view of these factors, the skilled artisan would adjust the particular dose as necessary. In general, the formulation of a composition of the invention and the routes and frequency of administration are determined, initially, using Phase I and Phase II clinical trials.

The pharmaceutical composition can be formulated for oral formulation, such as a tablet, or a solution or suspension form; or can comprise an admixture with an organic or inorganic carrier or excipient suitable for enteral or parenteral applications, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes may be used, for example a stabilizing dry agent such as triulose (see, for example, U.S. Pat. No. 5,314,695).

A chimeric pro-caspase or an encoding polynucleotide can be administered to a subject in order to reduce the severity of a pathologic condition in the subject by inducing apoptosis of cells involved in the pathologic condition. For example, the cells associated with a pathologic condition can be characterized, in part, by the misexpression of a cell growth protein, and the chimeric pro-caspase can be designed such that oligomerization is effected due to its interacting specifically with the cell growth protein. Cancer, for example, fundamentally is a disease of uncontrolled cell growth. In many cases, the cancer cells harbor oncogenic mutations that cause the switch for cell growth to be stuck in the "on" position. In particular, key protein kinases that are involved cell proliferation can be maintained in the aggregated state and, therefore, remain activated. Accordingly, the elements of such protein kinases can be used to prepare a chimeric pro-caspase of the invention, which can oligomerize with the protein kinase in the cancer cell and induce a apoptosis in the cells.

A chimeric pro-caspase useful in treating a cancer patient, for example, can comprise an oligomerizing domain that interacts specifically with a Ras protein expressed in the cancer cells. Mutated Ras oncogenes are present in approximately thirty percent of human cancers. More specifically, Ras is mutated in about 25% to 30% of lung cancers, 50% of colon cancers, and 90% of pancreatic cancers, which are the first, third and fourth leading causes, respectively, of cancer death in the United States. In addition, even in cancers that are not characterized by overt Ras mutations, elevated Ras activity contributes to tumor growth. For example, the Her2/neu oncogene, which is overexpressed in aggressive breast cancers, triggers cancer cells to divide by signaling through Ras.

Ras transmits its growth signal, in part, by aggregating with the Raf kinase (Luo et al., *Nature* 383:178–181 (1996), which is incorporated herein by reference). As such, a chimeric pro-caspase comprising an oligomerizing domain based on a Ras-associating domain of Raf can respond specifically to activated Ras in cancer cells. Similarly, a chimeric pro-caspase can comprise an oligomerizing domain based on a Ras-associating domain of a guanine nucleotide exchange factors GEF can oligomerize with Ras in a cell, thereby activating apoptosis in the cell. Such chimeric pro-caspases, which can further comprise, for example, a membrane localization domain (see U.S. Pat. No. 5,776,689), can kill cells characterized, at least in part, by excessive Ras activity, thereby providing a therapeutic benefit for patients suffering from a number of common human cancers.

For treatment of a subject in vivo, a chimeric pro-caspase can comprise, for example, a peptide ligand domain, which binds a specific receptor expressed by the target cell (i.e., the cell involved in the pathologic condition); a protein transduction domain, which facilitates translocation into the cell; a cell compartmentalization domain, which localizes the chimeric pro-caspase to the appropriate cell compartment, or the like. In performing a method of the invention, the chimeric pro-caspase or encoding polynucleotide can be administered alone to the subject, or can be administered in combination with another therapy useful for treating the condition. For example, as disclosed herein, a polynucleotide encoding a chimeric pro-caspase comprising an oligomerizing domain that interacts specifically with Ras can be administered to a subject having a cancer characterized, in part, by over-expression or increased activity of Ras, thereby reducing the severity of the cancer. In addition, the subject can be treated using more routine methods, including, for example, by treatment with an appropriate chemotherapeutic agent.

A method of the invention similarly can be useful for reducing the severity of a viral infection, which are characterized, in part, by the expression of viral proteins in cells associated with the pathologic condition. For such a method, the chimeric pro-caspase is designed with an oligomerizing domain that interacts specifically with a polypeptide expressed by the virus or in response to viral infection of the cell. As such, the chimeric pro-caspase only oligomerizes in the virally infected cells, thereby restricting apoptosis only to those cells involved in the pathology.

In one embodiment, the invention provides a method of gene therapy. An advantage of a gene therapy method of the invention is that expression of the chimeric pro-caspase need only occur for a short period of time, since, upon oligomerization, apoptosis of the cell occurs. Thus, a gene therapy method of the invention is distinguishable from more typical gene therapy methods, where prolonged expression of the exogenously introduced gene product is required for a therapeutic effect.

In addition, a method of the invention can supplement current gene therapy procedures. For gene therapy, the exogenous nucleic acid molecule can be introduced into a patient either in vivo, in which the desired gene is administered directly to the patient, or ex vivo, in which cells are removed from the patient, transfected with desired genes, then transplanted back into the patient (see U.S. Pat. No. 5,399,346, which is incorporated herein by reference). A challenge of gene therapy is to develop safe and efficient methods for delivering an exogenous nucleic acid molecule into a cell (see, for example, Anderson et al., supra, 1998; Verma and Somia, supra, 1997; Wilson, supra, 1996). In particular, it can be necessary to ablate a genetically modified cell if the introduction of the exogenous nucleic acid molecule results in an unexpected and undesirable side effect.

Various methods have been utilized to ablate genetically modified cells following introduction of an exogenous nucleic acid molecule. In one method, a gene therapy vector can include an inducible suicide gene, such as the herpes simplex virus thymidine kinase (HSV-TK) gene. Cells containing the HSV-TK gene can be killed by treating the cells with the nucleoside analog, ganciclovir, which the HSV-TK gene product converts to an intermediate that can be incorporated into elongating DNA and results in death of the cells (Moolten, *Cancer Res.* 46:5276–5281 (1986)). Due to its mechanism of action, however, HSV-TK only kills proliferating cells and, therefore, it is not useful where the target cells for gene therapy are in a resting state. In addition, the HSV-TK gene is not a human gene and, therefore, the HSV-TK gene product can be immunogenic to the host.

The death receptor, Fas, also has been used as an agent to kill cells. Aggregation of Fas due to an interaction with its ligand can trigger apoptosis in proliferating and non-proliferating cells (Nagata and Goldstein, *Science* 267:1449–1456 (1995); Nagata, *Cell* 88:355–365 (1997)). A conditional Fas allele has been made with human FK506 binding protein (FKBP), and binds to a number of natural and synthetic ligands with high affinity. Dimers of these ligands can induce aggregation of fusion proteins that contain FKBP. A fusion polypeptide consisting of FKBP and Fas (FKBP-Fas) allows Fas to be aggregated by dimeric ligands, leading to cell death (Amara et al., supra, 1997; Clackson et al., supra, 1998; Spencer, supra, 1996). Since the FKBP-Fas consists of human proteins, it is non-immunogenic to a human host. However, many cell types are insensitive to Fas-mediated apoptosis and some cells are stimulated to proliferate upon treatment with Fas (Nagata and Goldstein, supra, 1995; Nagata, supra, 1997), thus limiting the usefulness of Fas as a means to ablate genetically modified cells.

The present invention provides chimeric pro-caspases, which can oligomerize in a cell and, therefore, can be used to selectively induce apoptosis in cell. As such, a polynucleotide encoding a chimeric pro-caspase can be included in a vector with an exogenous gene to be introduced into cells of the subject, or can be introduced in a second vector in combination with the gene therapy vector. Where it is desirable to ablate the cells containing the introduced gene therapy vector, for example, due to the termination of the treatment or due to the incorporation of exogenously introduced gene into a region of the genome such that a deleterious effect is produced, the co-introduced chimeric pro-caspase can be expressed in the cells, thereby activating caspase activity in the cells and inducing apoptosis. Such a method provides substantial advantages over the HSV-TK and Fas systems in that caspase activation leads to effective cell death in proliferating cells or non-proliferating cells, and in that the components of the pro-caspase constructs are human proteins, which should not substantially elicit an immunological response by the host.

The invention will now be described in greater detail by reference to the following non-limiting examples.

EXAMPLE I

Autoproteolytic Activation of Pro-capases by Ogliomerization

This example demonstrates that oligomerization of pro-caspases induces proteolytic generation of mature caspase subunits and activation of their cell death activity.

Expression Plasmids

FKBP12 and FasEC fusions of caspases were constructed in pRK5. For FKBP12 fusions, a fragment containing three tandem repeats of FKBP12 with an N-terminally fused c-Src myristylation signal and a C-terminally fused HA tag was amplified by polymerase chain reaction (PCR) from pMF3E (Spencer et al., *Science* 262:1019–1024 (1993), which is incorporated herein by reference), digested with EcoRI and BamHI, and cloned into pRK5, yielding pFkp3-HA. DNA fragments containing full-length and deletion mutants of human pro-caspase-8 with a C-terminal FLAG tag were digested with BamHI and HindIII and cloned into pFkp3-HA. pFkp3 was made by deleting the SalI/XhoI fragment of caspase-8(180) in pFkp3-Casp8(180).

Murine FasEC (residues 1–189) fusions were made by three-way ligation. For FasEC-Casp1, a BamHI/NcoI fragment of FasEC was ligated to a NcoI/SalI fragment of murine caspase-1 in pRK5. For FasEC-Casp3 and FasEC-Casp8(182), a BamHI/EcoRI fragment of FasEC was ligated with a EcoRI/SalI fragment of human caspase-3 or human caspase-8 residues 182–479 in pRK5. Active site cysteine to serine mutants were made by PCR mutagenesis and assembled as for the corresponding wild-type constructs. Each construct was confirmed by partial DNA sequencing and immunoblotting or in vitro translation. pRK-crmA (Hsu et al., *Cell* 81:495–504 (1995), which is incorporated herein by reference) and pEBB-mFas (Yang et al., *Cell* 89:1067–1076 (1997), which is incorporated herein by reference) were as described.

Cell Death Assay

The cell death assay was performed essentially as previously described (Yang et al., supra, 1997). $1.5 \times 10^5$ HeLa cells/well were transfected by the calcium phosphate precipitation method. For each transfection, 0.25 µg of a β-galactosidase reporter plasmid pCMV-lacZ was included and the total amount of DNA was adjusted to 1.25 µg with the vector plasmid pRK5. AP1510 dimerizing agent or monomeric FK506 competitor (Ariad Pharmaceutical, Inc.; Cambridge Mass.) was added 6 hr after transfection as indicated and cells were stained with X-gal 16 hr after transfection. For FasEC fusions, Jo2 antibody (PharMingen; San Diego Calif.) was added as indicated 10 hr after transfection, and cells were stained with X-gal 18 hr after transfection. The percentage of apoptosis was determined by counting the number of blue cells with apoptotic morphology and dividing by the total number of blue cells. Specific apoptosis was calculated as the percentage of apoptosis in each transfection minus the percentage of apoptosis in the vector-transfected cells that was not treated with either AP1510 or Jo2. The vector control was included in each experiment and showed less than 5% apoptosis. Data shown are the averages and standard deviations of 2 to 4 independent experiments. For each experiment, 200 or more blue cells were counted from randomly chosen fields.

Pro-Caspase Processing in Transfected Cells $7.5 \times 10^5$ 293T cells plated on 35 mm dishes were transfected with 1 μg of the indicated expression plasmids by the calcium phosphate method. Eleven hr after transfection, the medium from parallel transfections was exchanged for medium containing either vehicle or 1 μM AP1510. At the indicated time points, the transfected cells were washed once with ice cold PBS and extracted in 100 μl of IP-lysis buffer (Hsu et al., supra, 1995). Protein concentrations in extracts were equalized by the Bradford assay and analyzed by immunoblot for FLAG with ECL (Amersham; Uppsala Sweden; anti-FLAG MAb M2; Kodak; Rochester N.Y.; rabbit polyclonal anti-FLAG (Santa Cruz Biochemical Co.; Santa Cruz Calif.).

Cell-Free Processing of Pro-Caspase-8

In vitro transcription and translation of the indicated constructs with $^{35}$S-labeled methionine were carried out with the TNT Reticulocyte Lysate System (Promega; Madison Wis.). The reaction mixture contained 1 μl of the in vitro translation product and the indicated drugs dissolved in 3 μl of CED3 reaction buffer (Xue et al., Genes Devel. 10:1073–1083 (1996), which is incorporated herein by reference). Final drug concentrations of 100 nM of AP1510 or FK506 and 10 μM of Z-Asp-Glu-Val-Asp(SEQ ID NO:1) (Z-DEVD; Enzyme System Products; Calif.) were used. The reaction mixture was incubated in 30° C. for 4 hr, then the reaction stopped by the addition of SDS sample buffer. Reaction products were visualized by SDS-PAGE and autoradiography.

Apoptosis Mediated by Pro-Caspase8 Requires Its DED Domains

Overexpression of full-length pro-caspase-8 potently induces cell death (Boldin et al., supra, 1996; Muzio et al., supra, 1996). Since DED domains can mediate homophilic interactions, the ability of DED domains to oligomerize pro-caspase-8 molecules and activate them was examined. Wild-type pro-caspase-8 and mutants missing the DED domains were fused to a protein motif that allowed inducible oligomerization. Each fusion protein contained three tandem repeats of the FK506 binding protein (see FIG. 1A; "Fkp"), which is induced to oligomerize by addition of the divalent small chemical ligand such as AP1510 (Amara et al., supra, 1997). To facilitate membrane localization and product detection, fusion proteins carried an N-terminal c-Src myristylation signal and contained a hemagglutinin (HA) tag and a FLAG tag at the fusion junction and the C terminus, respectively; the C-terminal epitope tag does not interfere with p10 generation or caspase function (Xue et al., supra, 1996).

Figure 1B:
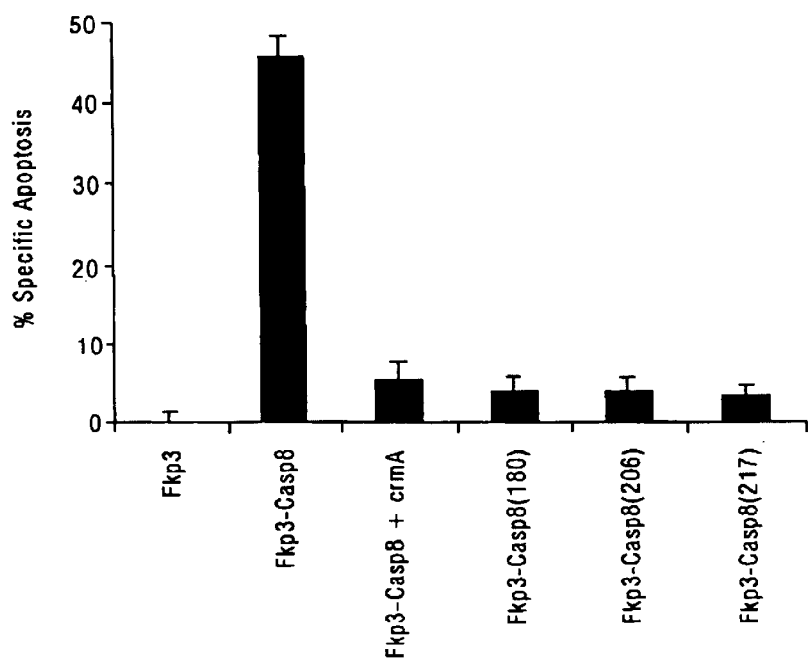

In the absence of the dimerizing agent (AP1510), expression of Fkp3-Casp8 in HeLa cells potently induced apoptosis (FIG. 1B). The apoptotic cells showed the characteristic morphologies of membrane blebbing, pyknosis, and rounding up of the cell body. The cell death activity of Fkp3-Casp8 was blocked by the poxvirus serpin inhibitor, crmA, consistent with previous results (Boldin et al., supra, 1996; Muzio et al., supra, 1996). In contrast to the full length pro-caspase-8 fusion, three mutants that lack the DED domains demonstrated much-reduced apoptosis ( 1B), indicating that the DED domains of pro-caspase-8 are required for its cell death activity.

Activation of Pro-Caspase-8 by FKBP-Mediated Oligomerization

Figure 2A:
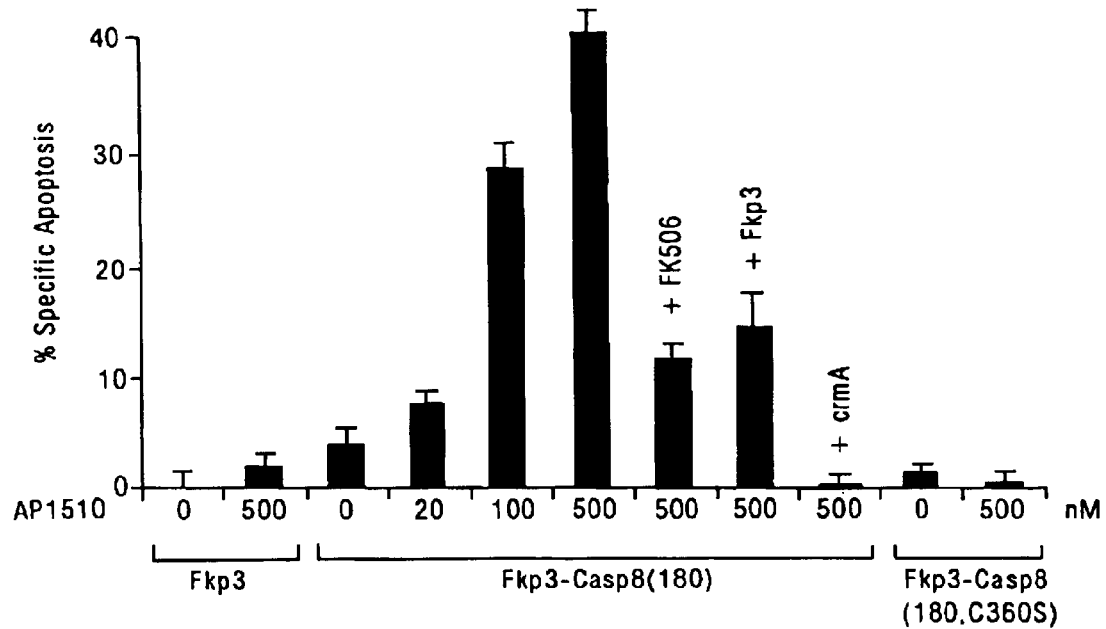
FIGS. 2A and 2B show that oligomerization of the protease domain of pro-caspase-8 induces apoptosis.

If the function of DED domains is to oligomerize pro-caspase-8 molecules, then oligomerization of the Fkp3-caspase-8 mutants by AP1510 should restore their apoptotic activity. Fkp3-Casp8(180) caused little cell death in the absence of the dimerizing agent (less than 5%; FIG. 1B and FIG. 2A). Addition of AP1510 caused a dose-dependent increase of apoptosis in HeLa cells expressing Fkp3-Casp8 (180). Similar results were observed when 293T cells were used for transfection. At an AP1510 concentration of 500 nM, more than 40% of transfected cells underwent apoptosis (FIG. 2A), which is comparable to the level observed in cells expressing Fkp3-Casp8. Addition of the monomeric, competitive FKBP ligand, FK506, inhibited this apoptotic effect. In addition, Fkp3, which consists of only the tandem FKBP12 domains (FIG. 1A), caused a dominant-negative inhibition of killing induced by AP1510 (FIG. 2A). The cell killing induced by Fkp3-Casp8(180) also was inhibited by crmA. In a control experiment, mutation of the active site cysteine (C360S) in Fkp3-Casp8(180) abolished the apoptotic activity in the presence of dimerizing agent. These results demonstrate that oligomerization of the protease domain of pro-caspase-8 activates its killing activity and that cell death induced by oligomerization is dependent on the intrinsic caspase activity of caspase-8.

Figure 2B:
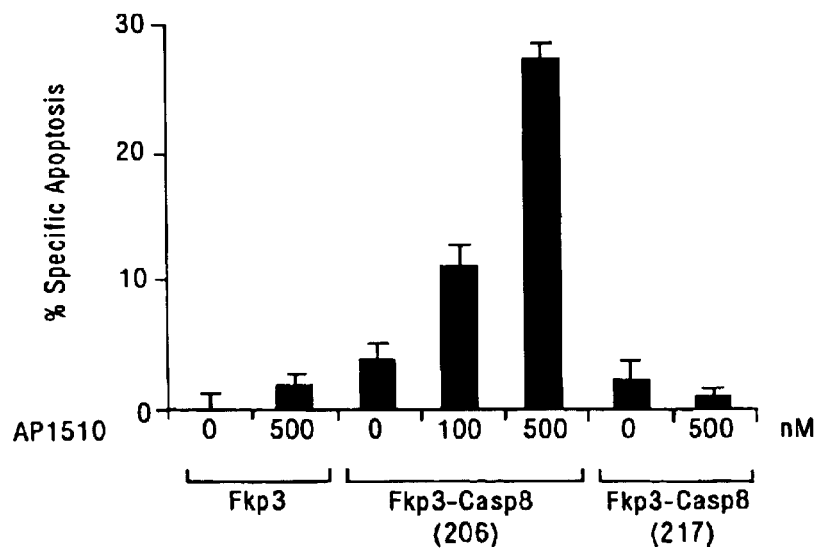

As with Fkp3-Casp8(180), the addition of AP1510 also activated the apoptotic activity of Fkp3-Casp8(206) (FIG. 2B). Both constructs contain residue Asp-216, which is recognized during the processing of pro-caspase-8 (Medema et al., supra, 1997). In contrast, killing by Fkp3-Casp8(217), which lacks this cleavage recognition residue, did not increase with the addition of AP1510 (FIG. 2B). This result indicates that pro-caspase processing at residue 216 may be required for generating active caspase and, therefore, for oligomerization-induced killing.

Fas Extracellular Domain-Mediated Oligomerization of Three Pro-Caspases

To confirm that oligomerization activates pro-caspase-8, an alternative strategy of inducing oligomerization through a membrane-bound receptor, using the extracellular domain of murine Fas (FasEC, FIG. 3A), was examined. The FasEC was used for these studies because of the availability of its agonistic antibody, Jo2, which is a pentameric IgM antibody that allows effective oligomerization (Ogasawara et al., Nature 364:806–809 (1993), which is incorporated herein by reference). Since Jo2 does not recognize human Fas, it has no toxic effect on human cell lines. In addition, by making a FasEC fusion of the protease domain of pro-caspase-8 (FasEC-Casp8(182)), several intermediaries that participate in the in vivo Fas-FADD-pro-caspase-8 connection, including the death domain of Fas, FADD, and the DED domains of pro-caspase-8, could be avoided. As such, the function of these protein motifs could be examined.

Addition of Jo2 did not cause cell death in human HeLa cells expressing FasEC (FIG. 3B). However, addition of Jo2 activated the apoptotic activity of FasEC-Casp8(182) in adose-dependent fashion (FIG. 3B). The level of cell death induced by FasEC-Casp8(182) was similar to the level induced by wild-type Fas at the maximal Jo2 concentration. Jo2-induced apoptosis through FasEC-Casp8(182) was blocked by crmA, and a catalytic cysteine-to-serine mutant, FasEC-Casp(182,C360S), did not respond to Jo2, again demonstrating that oligomerization-induced death required the intrinsic protease activity of the caspase. These results confirm the results obtained using the FKBP fusions and indicate that pro-caspase-8 can be activated by oligomerization. The results further indicate that the intermediary protein motifs between Fas and pro-caspase-8 act to physically link the pro-caspase-8 protease domain to the ligand-binding extracellular domain of Fas, thus resulting in activation of pro-caspase-8.

Figure 3C:
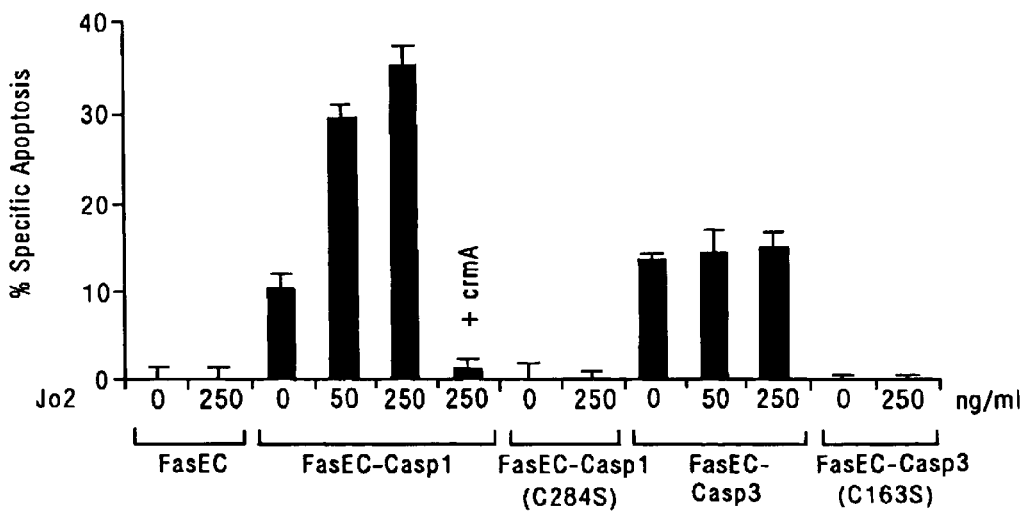

Pro-caspase-1 and -3 also were examined using the FasEC fusion system in order to determine whether oligomerization-induced activation is a general property of caspases. Pro-caspase-1contains a long prodomain, similar to pro-caspase-8, but has a different substrate specificity (Thornberry et al., *J. Biol. Chem.* 272:17907–17911 (1997)). In comparison, pro-caspase-3 contains a very short prodomain, but its substrate specificity overlaps with that of caspase-8 (Thornberry et al., supra, 1997). Similarly to the results observed for pro-caspase-8, Jo2 activated apoptosis by a fusion of FasEC with pro-caspase-1 (FasEC-Casp1) in a dose-dependent manner (FIG. 3C). In comparison, FasEC-Casp1(C284S), in which the catalytic cysteine was mutated, caused no death even in the presence of Jo2, demonstrating that intrinsic caspase-1 protease activity was required for apoptosis to occur.

In contrast to the results obtained using pro-caspase-1and pro-caspase-8, a FasEC fusion of pro-caspase-3, FasEC-Casp3, failed to respond to Jo2 in killing cells, even though FasEC-Casp3 caused substantial cell death by itself (FIG. 3C). Similarly to the fusions of the other two proteases, FasEC-Casp3(C 163S) caused no killing, indicating that killing by FasEC-Casp3 also required its intrinsic protease activity. Thus, FasEC-Casp3 is not activated by oligomerization, but may be activated by pre-existing cellular caspases. These results indicate that oligomerization-induced activation may be a property of initiator caspases, but not of executioner caspases.

Induction of Pro-Caspase Processing by Oligomerization

Oligomerization-induced apoptosis was further characterized by examining the fate of pro-caspase proteins in transfected cells with and without induced oligomerization. 293T cells were used in these experiments because of their high transfection efficiency. At DNA concentrations that allow detection of transfected gene products by immunoblotting, Fkp3-Casp8(180) induced some apoptosis and was slowly processed in the absence of dimerizing agent (FIG. 4A, lanes 1–5). The slow processing may represent the basal probability of membrane-targeted Fkp3-zymogen molecules randomly encountering one another.

Processing generated two peptides containing the C-terminal FLAG-epitope: p37 (labeled ΔN), which appeared first, and p10. p10 likely corresponds to the small subunit in mature caspase-8 (Medema et al., supra, 1997), which is derived from the C terminus of pro-caspase-8, and p37 is a processing intermediate. In contrast, when Fkp3-Casp8(180) was expressed in the presence of AP1510, the zymogen was completely processed after only 1 hour of treatment with dimerizing agent, and only ΔN was completely processed after 2 hours of dimerizing agent treatment (FIG. 4A, lane 7). In the presence of the dimerizing agent, newly synthesized zymogen was rapidly processed and accumulated as ΔN and p10 FIG. 4A, lanes 8–10). This result indicates that oligomerization induces the processing of Fkp3-Cas8(180). Moreover, processing required the intrinsic caspase activity of the zymogen. The active site C360S mutant of Fkp3-Casp8(180) did not become processed, even in the presence of AP1510 (FIG. 4A, lanes 11–12). Thus, oligomerization does not result in pro-caspases become better substrates for a pre-existing cellular caspase but, instead, pro-caspase processing is an autoproteolytic process. These results correspond with the observation that deletion of one caspase recognition site in Fkp3-Casp8(217) blocked processing induced by AP1510 (FIG. 4A, lanes 13 and 14), since the caspase retained the ability to oligomerize.

The ability to detect p10was unexpected because cell death occurs quickly upon generation of active caspase-8 in the cytosol. As such, the p10 detected in these experiments likely remains bound to the membrane-targeted Fkp3-zymogen oligomer. In the course of generating the mature tetrameric caspase from two zymogen molecules, one zymogen may be processed before the other, producing p20 and p10 subunits that are bound to unprocessed zymogens. As such, p10 is detected in dimerizer-treated cells only when there is also some low level of the full-length zymogen (FIG. 4A, lanes 9 and 10). The cowpox virus serpin inhibitor crmA does not affect pro-caspase-8 processing, but inhibits mature caspase-8 activity (Medema et al., supra, 1997; Muzio et al., supra, 1997). When crmA was coexpressed with Fkp3-Casp8(180), processing was significantly slowed, and the processing intermediate ΔN was observed only in the presence of AP1510 (FIG. 4B).

To circumvent the limitations of intracellular expression experiments, a cell-free system was established, in which pro-caspase processing could be initiated by inducing oligomerization. The addition of AP1510 to in vitro translated, $^{35}$S-labeled Fkp3-Casp8(206) led to the proteolytic generation of peptides corresponding to the mature caspase-8 subunits p18 and p10, and three processing intermediates p46, p37, and p20 (FIG. 5A). Processing initiated by AP1510 was blocked by the addition of FK506, the monomeric ligand of FKBP that competes for AP510 binding, and also was inhibited by the addition of the caspase inhibitor z-DEVD (SEQ ID NO:1, FIG. 5A). These results demonstrate directly that pro-caspase processing in vitro requires oligomerization and caspase activity. Fkp3-Casp8(2 17) served as a negative control and was incapable of being processed in the presence of AP1510 (FIG. 5A). In the absence of the in vitro translated pro-caspase, the reaction mixture contained no caspase activity, as demonstrated by the lack of PARP cleavage in the presence of AP1510.

Figure 5B:
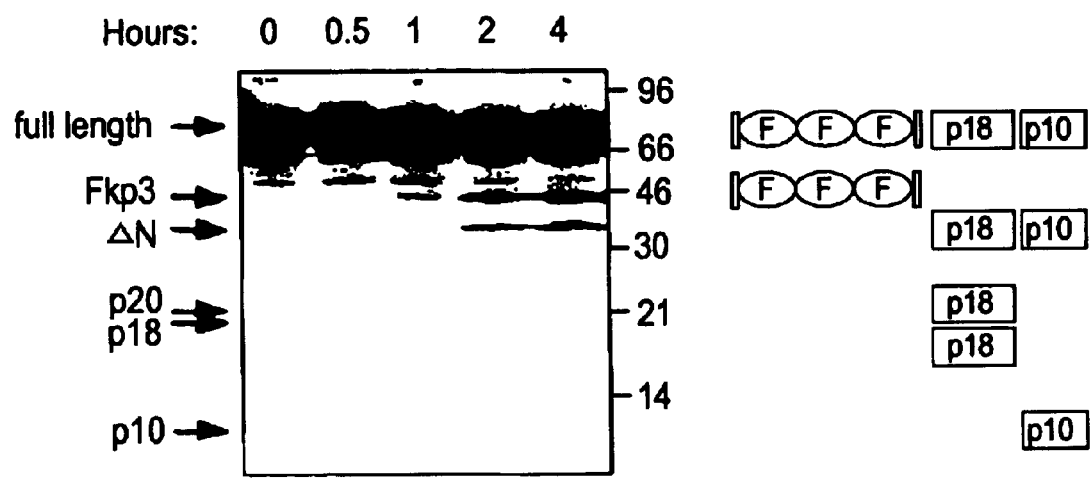

Based on time course experiments (FIG. 5B), relative band intensities normalized by the known methionine content of the predicted peptides, comigration with known truncation mutants, and the presence of the C-terminal FLAG epitope tag, the identities of the proteolytic products tentatively could be assigned (FIG. 5B) and a model of pro-caspase processing identified. First, the prodomain was separated from the protease domain, generating p46 and p37. p46 corresponded to the N-terminal Fkp3, and p37 corresponded to ΔN (see FIG. 4) and consisted of the protease domain. Second, the protease domain was cleaved to generate p20 and p10. p20 then was processed to p18. p18 and p10 are the mature subunits of caspase-8 that can associate to form a tetrameric enzyme. Consistent with this sequence of cleavages, deletion of the predicted first cleavage site in Fkp3-Casp8(217) completely blocked processing (FIG. 4A, FIG. 5A). Taking FKBP-fused pro-caspase-8 as a model, these results collectively demonstrate that oligomerization induces autoproteolytic processing of pro-caspases in vivo and in vitro.

EXAMPLE II

Preparation and Characterization of Chimeric Pro-Caspase

This example describes the construction and characterization of viral vectors expressing an FKBP-pro-caspase fusion polypeptide that can effectively induce apoptosis upon oligomerization, but that otherwise demonstrates minimal autotoxicity.

For oligomerization of caspases to be an effective suicide system, the caspase should have maximal cytotoxicity in the presence of a dimerizing agent, but minimal cytotoxicity in the absence of the dimerizer. The human FKBP protein is used for the oligomerization motif. The efficacy of FKBP dimerization has been demonstrated in various cells for diverse biological processes (Spencer et al., supra, 1993; Amara et al., supra, 1997; Freiberg et al., *J. Invest. Dermatol.* 108:215–219 (1997); Freiberg et al., *J. Biol. Chem.* 271:31666–31669 (1996); Holsinger et al., *Proc. Natl. Acad. Sci., USA* 92:9810–9814 (1995)). To minimize the binding of dimeric ligands to endogenous FKBP, the FKBP-ligand interface was redesigned to generate a ligand, AP1903, which is specific to a FKBP derivative Fv (Clackson et al., supra, 1998)). AP1903 and Fv are available from Ariad pharmaceutical, Inc. Two copies of Fv are fused to the pro-caspase (see FIG. 6) to facilitate oligomerization; using more copies of Fv was not necessary (Clackson et al., supra, 1998).

Numerous caspases have been cloned, and the selection of a caspase for use in a cell suicide system is based, on several factors. For example, the caspase should have substrate specificity similar to the executioner caspase to ensure cleavage of cellular substrates. In addition, the presence of a pro-domain, which sometime mediates homotypic interaction among pro-caspase molecules, can be useful because it can enhance the oligomerization. At high expression level, however, the presence of prodomain may result in autotoxicity. Caspase-8 is particularly useful because it has substrate specificity similar to caspase-3, which cleaves most cell death substrates identified so far. Caspase-8 contains within its pro-domain two DED domains, which can interact homotypically. The *C. elegans* caspase CED-3 is another useful caspase because, similarly to caspase-8, it effectively cleaves cellular substrates and its pro-domain can self-associate. The nucleic acid construct is cloned into a retroviral expression vector or other viral vector commonly used for long term expression of transgene.

Figure 6:
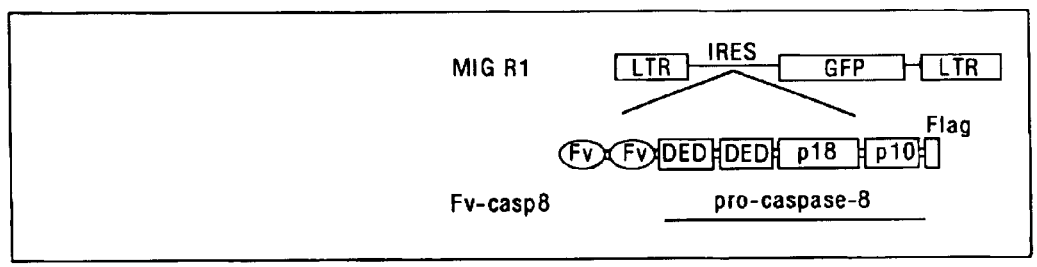
FIG. 6 illustrates the green fluorescent protein-(GFP-) expressing MSCV retrovirus, MIG R1, and the construct encoding the Fv-caspase-8 fusion polypeptide. DED, death effector domain; p18 and p10, the large and small subunits that form mature caspase-8; Flag, the FLAG epitope tag, which facilitates detection of protein by immunoblotting; IRES, internal ribosome entry site; LTR, retrovirus long terminal repeats. Sequence encoding "pro-caspase-8" is indicated. An Fv fusion that contains the entire, partial, or no prodomain can be made.

Full length or various mutants of pro-caspase-8 or any other selected caspase is fused to two copies of Fv in the murine stem cell virus (MSCV) retroviral vector, MIG R1 (FIG. 6; Pear et al., *Blood* 92:3780–3792 (1998), which is incorporated herein by reference). The retroviral LTR of MSCV provides high level protein expression in various cells, including embryonic carcinoma and embryonic stem cells, and the presence of extended retroviral package sites in MIG R1 allows maximal retroviral production. A humanized green fluorescent protein expressed from an internal ribosomal entry sites allows visualization and fluorescence activated cell sorting (FACS) analysis of transduced cells (see FIG. 6).

For viral production, vectors expressing Fv-caspase-8 fusion polypeptides (Fv-casp8) are transfected into BOSC cells, which is a packaging cell line derived from the highly transfectable 293 cell line. BOSC cells can produce high titer, helper virus-free retroviruses within 48 hr (Pear et al., *Proc. Natl. Acad. Sci. USA* 90:8392–8396 (1993), which is incorporated herein by reference). The Fv-casp8 expressing viruses produced in the BOSC cells are harvested and used to infect 3T3 cells.

Autotoxicity of Fv-casp8 viruses is evaluated by comparing the percentage of apoptotic cells in Fv-casp8 virus-infected 3T3 cells with the percentage in MIG R1-infected 3T3 cells. Percentage of apoptotic cells are counted as described by Yang et al. (supra, 1997). Apoptotic cells are identified by cell body shrinkage, membrane blebbing, and detachment from plates. Transfected cells are identified by detecting the expression of GFP. Fv-casp8-expressing viruses that, without induction, cause only a low-level of cell death are selected. AP1903-induced apoptosis in Fv-casp8 transfected cells is assayed by culturing Fv-casp8-infected 3T3 cells in the presence of various concentration of AP1903. Percentage of apoptotic cells are counted and the Fv-casp8 expressing vectors that demonstrate high sensitivity to AP1903 are selected.

These experiments allow the selection of optimal Fv-casp8 constructs that demonstrate minimal autotoxicity in the absence of AP1903, but achieve maximal apoptosis when induced to oligomerize in the presence of AP1903. Furthermore, since caspases often act in a cascade, two genes can be introduced into a cell to be treated, including a gene encoding an Fv-caspase fusion, which serves as a initiator caspase, and a gene that acts as an executioner caspase to amplify the cell death signal.

The selected Fv-caspase vectors are examined using an in vivo model system. Viral vectors expressing the optimal Fv-casp8 fusion are used to infect mouse bone marrow cells, then the transfected cells are used to reconstitute lethally irradiated recipient mice. The use of a reconstitution assay allows an assessment of whether 1) the Fv-casp8 transgene interferes with development and differentiation of infected stem cells, and 2) AP1903 can kill, in vivo and in vitro, various lineage cells derived from the infected bone marrow cells. A murine chronic myelogenous leukemia model has been established using a similar procedure (Pear et al., *Blood* 92:3780–3792 (1998), which is incorporated herein by reference). The efficacy of the optimal Fv-casp8 vector then will be examined by infecting tumor cells with the Fv-casp8 expressing viruses, transplanting the infected tumor cells into mice, administering AP1903 to the mice, and monitoring tumor formation.

For bone marrow transplantation, donor mice are primed with 5-fluorouracil. Bone marrow cells are isolated and pre-incubated with interleukin-3 (IL-3), IL-6, and stem cell factor (SCF). The bone marrow cells then are co-cultivated with BOSC cells that have been transfected with Fv-casp8 vector. Infected marrow cells are selected by FACS sorting for GFP expression, and transplanted into lethally irradiated recipients. Hematopohesis in the recipient is followed closely. Expression of Fv-casp8 protein in hematopoietic tissues is examined by immunoblotting with anti-Flag monoclonal antibody. The myeloid and lymphoid lineages in the reconstituted recipient are examined for their functions and their sensitivity to AP1903. Cell death is examined by propidium iodide staining, followed by FACS analysis.

For tumor formation, MOPC-11 murine myeloma cells are infected with the Fv-casp8 viruses. Infected cells are isolated by FACS sorting and implanted in Balb/c mice. AP1903 is injected into the animals and tumor development is monitored. These experiments can demonstrate whether the Fv-casp8 transgene interferes with the functions of the infected cells and whether the infected cells are killed effectively in vitro and in vivo by AP1903.

While the invention has been described in detail with reference to the examples provided above, it will be understood that modifications and variations are within the spirit and scope of that which is described and claimed. Accordingly, the invention is limited only by the following claims.

What is claimed is:

1. An isolated polynucleotide encoding a chimeric pro-caspase comprising an initiator pro-caspase domain and a heterologuous oligomerizing domain capable of oligomerizing the initiator pro-caspase domain, wherein the initiator pro-caspase domain comprises a cleavage recognition site and the catalytic domain of an initiator caspase having autoactivation upon oligomerization.

2. The polynucleotide of claim 1, which is contained in a vector.

3. The polynucleotide of claim 2, wherein the vector is an expression vector.

4. The polynucleotide of claim 3, wherein the expression vector is a viral vector.

5. An isolated host cell containing the vector of claim 2.

6. The polynucleotide of claim 1, wherein the pro-caspase domain comprises pro-caspase-8.

7. The polynucleotide of claim 1, wherein the pro-caspase domain comprises a pro-capase from of an initiator caspase.

8. The polynucleotide of claim 1, wherein the pro-caspase domain is from a pro-caspase selected from pro-caspase-1, pro-caspase-2, and pro-caspase-8.

9. The polynucleotide of claim 1, wherein the oligomerizing domain comprises the FK506 binding protein.

10. A composition comprising an isolated polynucleotide according to claim 1 and a carrier.

* * * * *

SEQUENCE LISTING

<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: enzyme used in cell-free processing of
      Pro-Caspase-8

<400> SEQUENCE: 1

Glx Asp Glu Val Asp
 1               5